US008548594B2

(12) United States Patent
Thimineur et al.

(10) Patent No.: US 8,548,594 B2
(45) Date of Patent: *Oct. 1, 2013

(54) STIMULATION SYSTEM AND METHOD TREATING A NEUROLOGICAL DISORDER

(75) Inventors: Mark Thimineur, Orange, CT (US); Ed Kravitz, Milford, CT (US); Peter Lando, Plano, TX (US); Tracy Cameron, Toronto (CA); Rohan Hoare, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,146

(22) Filed: Feb. 28, 2012

(65) Prior Publication Data

US 2012/0158092 A1 Jun. 21, 2012

Related U.S. Application Data

(60) Continuation of application No. 12/762,789, filed on Apr. 19, 2010, now abandoned, which is a division of application No. 12/762,789, filed on Jul. 26, 2005, now Pat. No. 7,711,432.

(60) Provisional application No. 60/670,454, filed on Apr. 12, 2005, provisional application No. 60/628,680, filed on Nov. 17, 2004, provisional application No. 60/591,195, filed on Apr. 12, 2005.

(51) Int. Cl.
*A61N 1/36* (2006.01)

(52) U.S. Cl.
USPC .................................. 607/45; 607/2

(58) Field of Classification Search
USPC ........................................ 607/2, 45
See application file for complete search history.

(56) References Cited

U.S. PATENT DOCUMENTS

| 5,263,480 A | 11/1993 | Wernicke et al. |
| 5,299,569 A | 4/1994 | Wernicke et al. |
| 5,470,846 A | 11/1995 | Sandyk et al. |
| 5,540,734 A | 7/1996 | Zabara et al. |
| 5,776,170 A | 7/1998 | MacDonald et al. |
| 6,236,892 B1 | 5/2001 | Feler |
| 6,463,328 B1 | 10/2002 | John |
| 6,505,075 B1 | 1/2003 | Weiner |
| 6,721,603 B2 | 4/2004 | Zabara et al. |
| 6,735,475 B1 | 5/2004 | Whitehurst et al. |
| 6,788,975 B1 | 9/2004 | Whitehurst et al. |
| 7,493,172 B2 | 2/2009 | Whitehurst et al. |
| 7,711,432 B2 | 5/2010 | Thimineur et al. |
| 2003/0074032 A1 | 4/2003 | Gliner |
| 2003/0181958 A1 | 9/2003 | Dobak |
| 2003/0236557 A1 | 12/2003 | Whitehurst et al. |
| 2005/0065553 A1 | 3/2005 | Ben Ezra et al. |
| 2005/0154419 A1 | 7/2005 | Whitehurst et al. |
| 2006/0095088 A1 | 5/2006 | DeRidder |
| 2006/0206166 A1 | 9/2006 | Weiner |

*Primary Examiner* — Carl H Layno
*Assistant Examiner* — Jennifer Ghand

(57) ABSTRACT

According to one aspect, a stimulation system is provided for electrically stimulating a predetermined site to treat a neurological condition. The system includes an electrical stimulation lead adapted for implantation into a subcutaneous area in communication with a predetermined site, wherein the site is neuronal tissue that is associated with C2/C3 dermatome area, or stimulating cervical nerve roots and/or stimulating cranial nerves and/or stimulating any area associated with the occipital area. The stimulation lead includes one or more stimulation electrodes adapted to be positioned in the predetermined site. The system also includes a stimulation source that generates the stimulation pulses for transmission to the one or more stimulation electrodes of the stimulation lead to deliver the stimulation pulses to the predetermined site to treat a neurological disorder or condition.

9 Claims, 15 Drawing Sheets

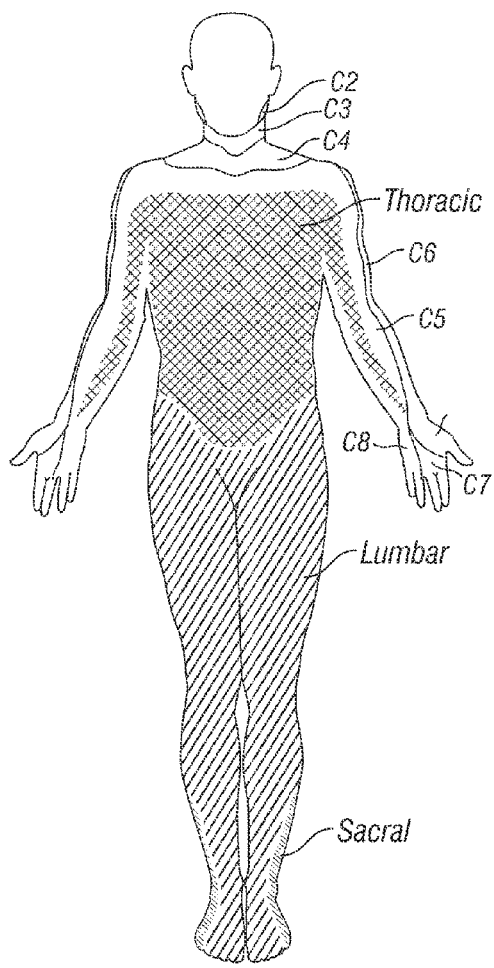
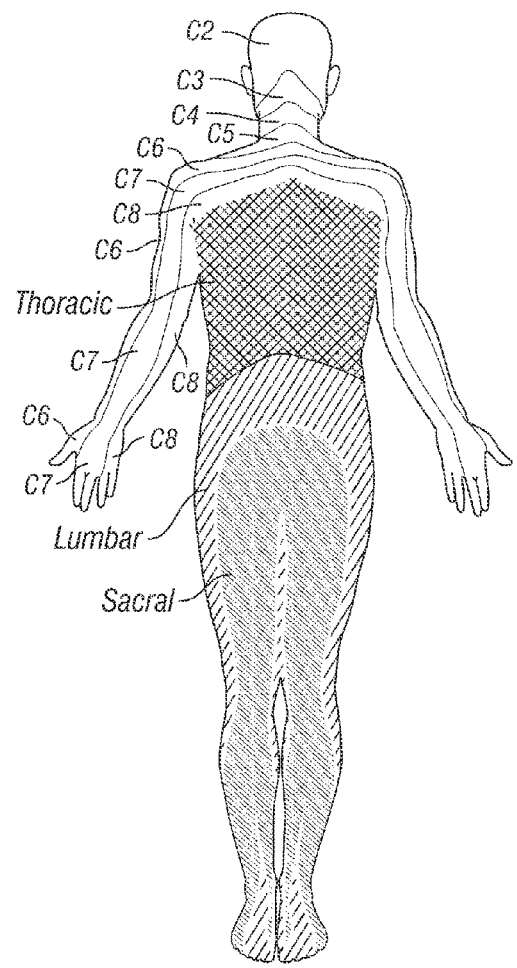
FIG. 3A-1
FIG. 3A-2

D Relative Power (%)

INTRAHEMISPHERIC: LEFT

|     | DELTA | THETA | ALPHA | BETA  |
|-----|-------|-------|-------|-------|
| FP1 | 17.72 | 14.99 | 16.99 | 50.30 |
| F3  | 18.89 | 20.69 | 24.55 | 35.88 |
| C3  | 16.65 | 20.47 | 35.12 | 27.76 |
| P3  | 15.55 | 16.74 | 36.36 | 31.34 |
| O1  | 10.31 | 12.36 | 36.03 | 41.30 |
| F7  | 33.62 | 20.44 | 25.61 | 20.34 |
| T3  | 17.66 | 15.03 | 41.94 | 24.37 |
| T5  | 14.27 | 12.46 | 35.17 | 39.08 |

INTRAHEMISPHERIC: RIGHT

|     | DELTA | THETA | ALPHA | BETA  |
|-----|-------|-------|-------|-------|
| FP2 | 29.03 | 22.27 | 23.96 | 24.75 |
| F4  | 24.55 | 24.27 | 27.74 | 23.43 |
| C4  | 21.63 | 20.48 | 31.41 | 26.48 |
| P4  | 17.01 | 17.12 | 40.13 | 26.74 |
| O2  | 12.34 | 13.75 | 36.29 | 37.62 |
| F8  | 46.47 | 21.54 | 17.91 | 14.08 |
| T4  | 23.64 | 18.95 | 32.70 | 24.71 |
| T6  | 16.83 | 15.28 | 38.76 | 29.13 |

Z Scored CD Relative Power

INTRAHEMISPHERIC: LEFT

|     | DELTA | THETA | ALPHA | BETA  |
|-----|-------|-------|-------|-------|
| FP1 | -0.01 | -0.50 | -1.90 | 4.96 |
| F3  | 0.74  | 0.21  | -1.43 | 2.51  |
| C3  | 0.75  | 0.73  | -0.90 | 9.95  |
| P3  | 0.92  | 0.61  | -1.30 | 2.11 |
| O1  | 0.36  | 0.28  | -1.58 | 4.38 |
| F7  | 2.80 | 0.49 | -1.35 | -0.11 |
| T3  | 0.64  | 0.15  | 0.04  | -0.18 |
| T5  | 0.81  | -0.01 | -1.46 | 2.27 |

INTRAHEMISPHERIC: RIGHT

|     | DELTA | THETA | ALPHA | BETA  |
|-----|-------|-------|-------|-------|
| FP2 | 2.31 | 0.59 | -1.60 | 0.67 |
| F4  | 2.09 | 0.66 | -1.16 | 0.43 |
| C4  | 1.71  | 0.71  | -1.20 | 0.75  |
| P4  | 1.29  | 0.74  | -1.08 | 1.45  |
| O2  | 0.68  | 0.47  | -1.70 | 3.21 |
| F8  | 4.60 | 0.59 | -2.24 | -1.29 |
| T4  | 2.16 | 0.72 | -0.64 | -0.11 |
| T6  | 1.12  | 0.58  | -1.30 | 1.33  |

*D Relative Power (%)*

INTRAHEMISPHERIC: LEFT

|  | DELTA | THETA | ALPHA | BETA |
|---|---|---|---|---|
| FP1 | 12.82 | 15.87 | 20.61 | 50.70 |
| F3 | 12.20 | 16.87 | 23.57 | 47.37 |
| C3 | 11.99 | 15.21 | 34.11 | 38.88 |
| P3 | 11.42 | 12.93 | 35.23 | 40.41 |
| O1 | 10.55 | 12.54 | 41.12 | 35.79 |
| F7 | 24.49 | 18.41 | 27.46 | 29.63 |
| T3 | 9.33 | 12.56 | 38.54 | 36.56 |
| T5 | 8.89 | 11.47 | 38.70 | 40.95 |

INTRAHEMISPHERIC: RIGHT

|  | DELTA | THETA | ALPHA | BETA |
|---|---|---|---|---|
| FP2 | 20.04 | 23.07 | 25.50 | 31.39 |
| F4 | 16.80 | 25.09 | 29.81 | 28.50 |
| C4 | 14.77 | 19.61 | 35.16 | 30.45 |
| P4 | 12.38 | 16.29 | 41.49 | 29.92 |
| O2 | 10.83 | 14.06 | 36.32 | 38.78 |
| F8 | 24.05 | 20.66 | 29.02 | 26.26 |
| T4 | 12.46 | 16.15 | 37.26 | 34.13 |
| T6 | 9.89 | 13.04 | 38.69 | 39.38 |

*Z Scored CD Relative Power*

INTRAHEMISPHERIC: LEFT

|  | DELTA | THETA | ALPHA | BETA |
|---|---|---|---|---|
| FP1 | -0.80 | -0.37 | -1.62 | *5.04* |
| F3 | -0.49 | -0.35 | -1.52 | *4.41* |
| C3 | -0.12 | -0.10 | -0.99 | *2.74* |
| P3 | 0.18 | 0.05 | -1.39 | *3.69* |
| O1 | 0.44 | 0.31 | -1.27 | *3.38* |
| F7 | 1.20 | 0.13 | -1.20 | 1.35 |
| T3 | 0.71 | -.042 | -0.23 | 1.49 |
| T5 | -0.24 | -0.17 | -1.21 | *2.68* |

INTRAHEMISPHERIC: RIGHT

|  | DELTA | THETA | ALPHA | BETA |
|---|---|---|---|---|
| FP2 | 0.59 | 0.70 | -1.47 | 1.72 |
| F4 | 0.45 | 0.77 | -1.00 | 1.36 |
| C4 | 0.41 | 0.57 | -0.94 | 1.44 |
| P4 | 0.40 | 0.60 | -1.00 | *2.25* |
| O2 | 0.41 | 0.51 | -1.70 | *3.40* |
| F8 | 0.98 | 0.44 | -1.17 | 0.58 |
| T4 | -0.16 | 0.22 | -0.31 | 1.25 |
| T6 | 0.00 | 0.22 | -1.32 | *2.66* |

TBI DISCRIMINANT SCORE = 0.08

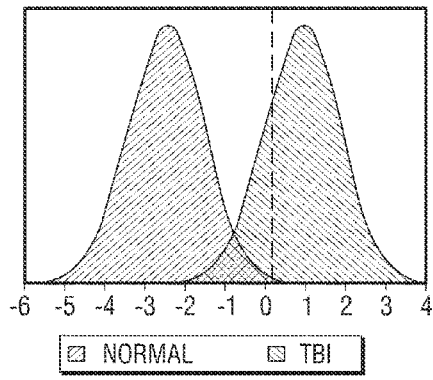

TBI PROBABILITY INDEX = 95.0%

|  |  |  | RAW | Z |
|---|---|---|---|---|
| FP1-F3 | COH | THETA | 79.15 | -0.59 |
| T3-T5 | COH | BETA | 35.10 | -1.04 |
| C3-P3 | COH | BETA | 67.96 | -1.33 |
| FP2-F4 | PHA | BETA | 0.02 | -1.43 |
| F3-F4 | PHA | BETA | 0.39 | -0.34 |
| F4-T6 | AMP | ALPHA | -33.21 | 0.06 |
| F8-T6 | AMP | ALPHA | 6.44 | 2.17 |
| F4-T6 | AMP | BETA | -21.78 | -0.72 |
| F8-T6 | AMP | BETA | 10.92 | 1.83 |
| F3-O1 | AMP | ALPHA | 76.03 | -0.08 |
| F4-O2 | AMP | ALPHA | -39.70 | 0.45 |
| F7-O2 | AMP | ALPHA | 95.57 | -0.29 |
| F4-O2 | AMP | BETA | -58.93 | -0.61 |
| P3 | RP | ALPHA | 36.36 | -1.30 |
| P4 | RP | ALPHA | 40.13 | -1.08 |
| O1 | RP | ALPHA | 36.03 | -1.58 |
| O2 | RP | ALPHA | 36.29 | -1.70 |
| T4 | RP | ALPHA | 32.70 | -0.64 |
| T5 | RP | ALPHA | 35.17 | -1.46 |
| T6 | RP | ALPHA | 38.76 | -1.30 |

*FIG. 6A-1*

TBI SEVERITY INDEX = 1.64

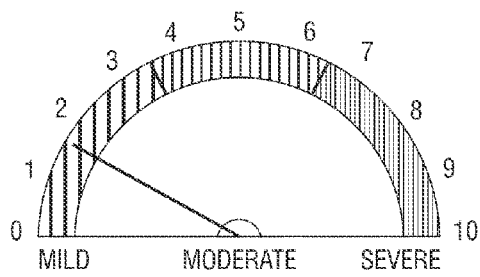

|  |  |  | RAW | Z |
|---|---|---|---|---|
| FP1-C3 | COH | DELTA | 42.10 | -1.03 |
| FP1-FP2 | COH | THETA | 82.92 | -0.55 |
| O1-F7 | COH | ALPHA | 36.24 | 0.20 |
| O2-T6 | COH | ALPHA | 76.53 | -1.12 |
| P3-O1 | COH | BETA | 69.99 | -0.55 |
| FP1-T3 | PHA | THETA | -6.22 | 0.67 |
| T3-T4 | PHA | THETA | 60.18 | 1.14 |
| O1-F7 | PHA | ALPHA | -42.45 | 1.04 |
| F7-F8 | PHA | ALPHA | 0.36 | -1.23 |
| T5-T6 | PHA | BETA | 1.17 | -0.72 |
| C3-F7 | AMP | DELTA | -56.89 | -2.77 |
| FP2-F4 | AMP | DELTA | 15.58 | 0.57 |
| C4-F8 | AMP | DELTA | -137.06 | -6.62 |
| O1-O2 | AMP | THETA | 13.74 | 0.85 |
| P3-F7 | AMP | ALPHA | 61.13 | -1.03 |
| FP2-P4 | AMP | ALPHA | -69.62 | 0.09 |

*FIG. 6A-2*

TBI DISCRIMINANT SCORE = 1.92

TBI PROBABILITY INDEX = NOT SIGNIFICANT

| | | | RAW | Z |
|---|---|---|---|---|
| FP1-F3 | COH | THETA | 77.60 | -0.81 |
| T3-T5 | COH | BETA | 34.34 | -1.99 |
| C3-P3 | COH | BETA | 52.23 | -3.61 |
| FP2-F4 | PHA | BETA | 0.45 | -0.31 |
| F3-F4 | PHA | BETA | 0.39 | -0.35 |
| F4-T6 | AMP | ALPHA | -26.18 | 0.22 |
| F8-T6 | AMP | ALPHA | -41.57 | 1.08 |
| F4-T6 | AMP | BETA | -29.76 | -0.95 |
| F8-T6 | AMP | BETA | -50.27 | 0.12 |
| F3-O1 | AMP | ALPHA | -48.32 | 0.38 |
| F4-O2 | AMP | ALPHA | -13.67 | 0.83 |
| F7-O1 | AMP | ALPHA | 76.63 | -0.66 |
| F4-O2 | AMP | BETA | -24.79 | 0.01 |
| P3 | RP | ALPHA | 35.23 | -1.39 |
| P4 | RP | ALPHA | 41.49 | -1.00 |
| O1 | RP | ALPHA | 41.12 | -1.27 |
| O2 | RP | ALPHA | 36.32 | -1.70 |
| T4 | RP | ALPHA | 37.26 | -0.31 |
| T5 | RP | ALPHA | 38.70 | -1.21 |
| T6 | RP | ALPHA | 38.69 | -1.32 |

STIMULATION SYSTEM AND METHOD TREATING A NEUROLOGICAL DISORDER

This application is a continuation of U.S. application Ser. No. 12/762,789, filed Apr. 19, 2010, which is a divisional of U.S. application Ser. No. 11/189,300, filed Jul. 26, 2005, now U.S. Pat. No. 7,711,432, which claims the benefit of U.S. Provisional Application Nos. 60/670,454 filed Apr. 12, 2005, 60/628,680 filed Nov. 17, 2004, and 60/591,195 filed Jul. 26, 2004, the disclosures of which are incorporated herein by reference in their entireties.

TECHNICAL FIELD

This invention relates to neuronal tissue stimulation for treating a neurological disorder, and more particularly to modulating neuronal tissue in the C2/C3 dermatome area, or stimulating cervical nerve roots and/or stimulating cranial nerves.

BACKGROUND OF THE INVENTION

Peripheral nerves are nerves in the body other than the nerves of the brain or spinal cord. Peripheral nerve injury may result in the development of chronic intractable pain. Some patients prove unresponsive to conservative pain management techniques. Peripheral Nerve Stimulation (PNS) has developed as a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical technique and patient selection have led to improved long term results.

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Another example of peripheral nerve stimulations include, for example, stimulating the C2 dermatome area to treat occipital neuralgia, which may be defined generally as an intractable headache originating in the back of the head in the vicinity of the C2 dermatome area (U.S. Pat. No. 6,505,075). This method of delivering electrical stimulation energy to the C2 dermatome area to treat occipital neuralgia involves positioning stimulation electrodes of an implantable electrical stimulation lead with at least one electrode in the fascia superior to in a subcutaneous region proximate the C2 dermatome area.

Yet further, the use of electrical stimulation for treating neurological diseases, including such disorders as movement disorders including Parkinson's disease, essential tremor, dystonia, and chronic pain, have also been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such electrical stimulation procedures include electroconvulsive therapy (ECT), repetitive transcranial (rTMS) magnetic stimulation and vagal nerve stimulation (VNS).

Traditional treatment options, for some forms of intractable pain (occipital pain, traumatic brain injury) that have proven to be resistant to medications, usually involve chemical, thermal or surgical ablation procedures following diagnostic local anesthetic blockade. Surgical approaches include neurolysis or nerve sectioning of either the C2 dermatome area in the occipital scalp or at the upper cervical dorsal root exit zone (extradural). Forammal decompression of C2 roots as well as C2 ganglionectomy have also been effective in reported cases. The present invention is the first to describe electrical stimulation to treat such conditions that are resistant to medications.

BRIEF SUMMARY OF THE INVENTION

The present invention involves a method and a therapeutic or stimulation system having a surgically implanted device in communication with a predetermined site, selected from the group consisting of C2 dermatome area, C3 dermatome area, cervical nerve roots (e.g., C1, C2, C3, C4, C5, C6, C7 and C8) and cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and hypoglossal nerve). The device is operated to stimulate the predetermined site thereby treating neurological disorder. The device can include a probe, for example, an electrode and/or an electrode assembly (e.g., electrical stimulation lead). The proximal end of the probe is coupled to a pulse generating source, (e.g., an electrical signal source), which, in turn, is operated to stimulate the predetermined treatment site. In certain embodiments, the probe and the pulse generating source are contained within the same unit, for example the Bion® stimulation system manufactured by Advanced Bionics Corporation. In addition, the system may include a means to program the pulse generating source, for example the means may include a device that allows for external programming, such as a hand-held device.

Magnetic stimulation of predetermined site for the treatment of neurological conditions is used in certain embodiments of the present invention. Magnetic stimulation can be provided by internally implanted probes or by externally applied directed magnetic fields. For example, transcranial magnetic stimulation (TMS), which involves the use of very short pulses of magnetic energy, can be used in the present invention, also known as repetitive transcranial (rTMS) magnetic stimulation.

According to one aspect, a neurological stimulation system is provided for electrically stimulating a predetermined site, for example a cervical dermatome area (e.g., C2 dermatome area, C3 dermatome area), cervical nerve roots and cranial nerves to treat one or more neurological disorders. The system includes an electrical stimulation lead adapted for implantation into a subcutaneous area in communication with the predetermined site for electrical stimulation of the predetermined site, more particularly the C2/C3 dermatome area. The stimulation lead includes one or more stimulation electrodes adapted to be positioned in the subcutaneous area of the predetermined site to deliver electrical stimulation pulses to the predetermined site. The system also includes a stimulation source that generates the electrical stimulation pulses for transmission to the one or more stimulation electrodes of the stimulation lead. Yet further, the system includes a means for programming the stimulation source, for example a handheld programmer can be used to externally program the stimulation source.

An electrical stimulation system having one or more stimulation electrodes is implanted subcutaneously such that one or more of the stimulation electrodes are in communication with the C2 and/or C3 dermatome area. More particularly, the stimulation electrodes are in communication with the C2 and/or C3 dermatome area or any of the branches or terminal branches of the C2 and/or C3 dermatome area located in the C2 and/or C3 dermatome area or any cervical nerve roots located in the C2 and/or C3 dermatome area and/or any cranial nerves that may be proximate or within or adjacent to the C2 and/or C3 dermatome area. The one or more stimulation electrodes deliver electrical stimulation pulses to the neuronal tissue of the C2 and/or C3 dermatome area, which thereby permanently or temporarily eliminates, reduces, or otherwise treats the one or more neurological disorders. This may in turn significantly increase the person's quality of life. Although occipital neuralgia may be treated in combination with the one or more conditions treated according to the present invention, in such a case the one or more conditions treated will include one or more conditions in addition to occipital neuralgia.

In certain embodiments, electrical stimulation of the predetermined site for example, C2 dermatome area, C3 dermatome area, cervical nerve roots and/or cranial nerves, may be provided to effectively treat pain. For example, in certain embodiments, electrical stimulation of the predetermined site may be provided to effectively treat fibromyalgia and/or chronic fatigue syndrome or other diffuse pain in any one or more regions of the body. As another example, in certain embodiments, electrical stimulation of the predetermined site may be delivered to treat localized, diffuse, or other pain in any one or more regions of the body below the head, such as pain in the neck, shoulders, upper extremities, torso, abdomen, hips, and lower extremities. As another example, in certain embodiments, electrical stimulation of the predetermined site may be delivered to treat Reflex Sympathetic Dystrophy (RSD) pain. As another example, in certain embodiments, electrical stimulation of the predetermined site may decrease the person's overall sensitivity to pain or increase the person's overall pain threshold, in certain cases significantly, such that the person experiences "total body" pain relief or other generalized pain relief throughout the body. For example, a person with a relatively low overall pain threshold may experience an elevation of the pain threshold from a relatively hyperalgesic state to a relatively normalized state, with concomitant pain relief throughout the body. Other example pain-related applications of electrical stimulation of the predetermined site in certain embodiments include: (1) treating post-operative pain associated with major surgery, perhaps using a temporary as opposed to a permanent stimulation lead (e.g., to augment or replace opioid analgesia); (2) treating focal pain (e.g., possibly in combination with electrical stimulation of the spinal cord or peripheral structures such as the periostium around the knee or hip); (3) treating pain in elderly patients with severe degenerative spinal or joint conditions (e.g., with additional improvements in sleep, cognition, and mood); and (4) treating trigeminal neuralgia. Yet further, the stimulation system of the present invention may result in pain relief in areas of the head not innervated by the C2 dermatome area and/or C3 dermatome area (such as outside the C2 dermatome area), for example, but not limited to pain in the face, ears, and mouth. These areas are innervated by the trigeminal nerve and other cranial nerves and those of the cervical plexus.

In certain embodiments, possibly in combination with one or more of the benefits described above, electrical stimulation of the C2 and/or C3 dermatome area and/or cervical nerve roots and/or cranial nerves may be provided to effectively treat impaired motor functioning. For example, in certain embodiments, electrical stimulation of the predetermined site may be provided to effectively treat lack of coordination in the upper or lower extremities (e.g., gait problems). As another example, in certain embodiments, electrical stimulation of the predetermined site may be provided to effectively treat motor disorders such as tremor (e.g., reducing the coarseness of tremor, and Parkinson's disease), dystonia (e.g., reducing the frequency and severity of torticollis or other forms of dystonia), restless leg syndrome and seizure.

In certain embodiments, possibly in combination with one or more of the benefits described above, electrical stimulation of the predetermined site may be provided to effectively treat other neurological disorders for example, but not limited to Developmental Disabilities [e.g., Cerebral Palsy, Mental Retardation, Attention Deficit Disorder (ADD), Pervasive Developmental Disorders and Autistic Spectrum Disorders (e.g., autism and Asperger's disorder), Learning Disabilities (e.g., dyslexia, disorders of motor functions (e.g., dysgraphia, dyspraxia, clumsiness), and nonverbal learning disabilities (e.g., dyscalculia, visuospatial dysfunction, socioemotional disabilities, and ADHD)]; Demyleinating Diseases [e.g., Multiple Sclerosis]; delirium and dementia [e.g., vascular dementia, dementia due to Parkinson's disease, dementia due to HIV disease, dementia due to Huntington's disease, and dementia due to Creutzfeld-Jakob disease; Alzheimer's dementia, multi-infarct dementia, stroke]; affective disorder [e.g., depression, mania, mood disorder, major depressive disorder, bipolar]; movement disorders [e.g, restless leg syndrome, Dyskinesia (e.g., tremor, dystonia, chorea and ballism, tic syndromes (e.g., Tourette's Syndrome), myoclonus, drug-induced movement disorders, Wilson's Disease, Paroxysmal Dyskinesias, Stiff Man Syndrome) and Akinetic-Ridgid Syndromes and Parkinsonism]; ataxic disorders [e.g., disturbances of gait]; substance abuse related disorders [e.g., alcohol use disorders, amphetamine use disorders, cannabis use disorders, caffeine induced disorders, cocaine use disorders, inhalant use disorders, opioid use disorders, hallucinogen disorders, sedative, hypnotic, or anxiolytic use disorders, and polysubstance use disorders]; sexual dysfunctions [e.g., sexual arousal disorder, male erectile disorder, female dyspareunia, male hypoactive disorder, and female hypoactive disorder]; eating disorders [e.g., overeating disorder, bulimia nervosa, and anorexia nervosa]; obesity, anxiety and obsessive compulsive disorder syndromes [e.g., anxiety, panic attacks, post-traumatic stress disorder, agoraphobia, obsessive and compulsive behavior]; impulse control disorders [e.g., pathological gambling, intermittent explosive disorder, kleptomania, and pyromania]; personality disorders (e.g., schizoid personality disorder, paranoid personality disorder, schizotypal personality disorder, borderline personality disorder, narcissistic personality disorder, histrionic personality disorder, obsessive compulsive personality disorder, avoidant personality disorder, dependent personality disorder, and anti-social personality disorder); and other psychiatric disorders [e.g., schizophrenia subtypes, schizoaffective disorder, schizophrenia undifferentiated, delusional disorder, cyclothymic disorder, somatoform disorder, hypochondriasis, dissociative disorder, and depersonalization disorder]; and Chiari I malformation.

In certain embodiments, the stimulation system of the present invention can be used to treat obesity and obesity related conditions and/or gastric motility conditions. The gastrointestinal disorders or conditions contemplated by the present invention include gastrointestinal altered motility, sensitivity and secretion disorders in which one or more of the symptoms and conditions affect the gastrointestinal tract from the mouth to the anus. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, menstrual cramps, pancreatitis, spastic and interstitial cystitis and ulcers and the visceral pain associated therewith. One with skill in the art is aware that any functional gastrointestinal disorder, including but not limited to those associated with gastric motility, is appropriate for treatment with the method and systems of the present invention. Eating disorders and conditions can include, but are not limited to obesity, anorexia nervosa, and bulimia nervosa. For example, it is contemplated that the method of the present invention may be used to treat a patient for obesity, binge eating, or compulsive overeating.

Yet further other conditions that can be treated include immune-diseases. Immune-mediated diseases include, for example, but not limited to, arthritis (e.g., rheumatoid arthritis and psoriatic arthritis), inflammatory bowel diseases (e.g., ulcerative colitis and Crohn's disease), endocrinopathies (e.g., type 1 diabetes and Graves disease), neurodegenerative diseases (e.g., multiple sclerosis, autistic spectrum disorder, Alzheimer's disease, Guillain-Barre syndrome, obsessive-compulsive disorder, optic neuritis, retinal degeneration, amyotrophic lateral sclerosis (ALS), Parkinson's disease, Huntington's Disease, Guillain-Barre syndrome, myasthenia gravis, and chronic idiopathic demyelinating disease (CID)), vascular diseases (e.g., autoimmune hearing loss, systemic vasculitis, and atherosclerosis), and skin diseases (e.g., dermatomyositis, systemic lupus erthematosus, discoid lupus erthematosus, scleroderma, and vasculitics). More specifically, the immune-mediated disorders that can be treated by the present invention include, but are not limited to rheumatoid arthritis, eryematos, Sojourn's syndrome, allergic asthma, atopic skin disease, chronic fatigue syndrome, allergies, and Chron's disease.

In certain aspects of the present invention, the stimulation system can be used to treat neuroendocrine disorders, such as disorders associated with the crosstalk that occurs between the endocrine system and the nervous system. More particularly, the stimulation system of the present invention can be used to treat disorders associated with the hypothalamic-pituitary-adrenal (HPA) and -gonadal (HPG) axes, as well as disorders associated with the autonomic nervous system. Diseases associated with the HPA axis can include, but are not limited to pituitary tumors, Cushing syndrome, adrenal insufficiency, ACTH resistance, Congenital Adrenal Hyperplasia (CAH), adrenocortical tumors, glucocorticoid resistance/hypersensitivity, and mineralocorticoid resistance. Diseases of the HPG axis can include, but are not limited to hypothalamic hypogonadism, disturbances of the menstrual cycle, ovarian and testicular gonadotropin resistance, endometriosis, and infertility. Disease associated with the autonomic nervous system can include, but are not limited to pheochromocytoma and catecholamine deficiency. Still further, developmental/psychiatric, metabolic and immune disorders related to the functions of the HPA and HPG axes and the autonomic system can include, but are not limited to premature adrenarche, eating disorders—including anorexia and bulimia nervosa and adolescent obesity—adolescent conduct disorder, dysthymia and depression, childhood asthma and rheumatoid arthritis, the premenstrual tension syndrome, and postpartum and climacteric depression and autoimmunity.

Still further, the stimulation system of the present invention can be used to provide stimulation to the predetermined sited to enhance or improve cardiac function, for example, hemodynamics, electrical activity, myocontractility, perfusion of the heart muscle, as well as enhance cardiac performance or efficiency, such as balance between supply and demand. Thus, the present invention can be used as a prophylactic system to enhance or improve cardiac function. The present invention may also be used to treat cardiovascular disorders which include but are not limited to diseases and/or disorders of the pericardium (i.e., pericardium), heart valves (i.e., incompetent valves, stenosed valves, Rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). Other symptoms that can be related cardiovascular diseases include cholesterol and/or blood pressure. Thus, the present invention can be used to decrease cholesterol levels and/or to regulate blood pressure, for example decrease blood pressure in a subject suffering from high blood pressure.

Yet further, the stimulation system of the present invention can be use to provide stimulation to the predetermined site to modulate blood glucose. Blood glucose can be used as an indicator of diabetes mellitus. Thus, it is envisioned that the present invention may be used to treat diabetes mellitus.

In certain embodiments, electrical stimulation of the predetermined area may effectively treat other conditions including intractable nausea, chronic fatigue, sleep disorders, sleep apnea, visceral disorders, such as irritable bowel or areas of the body supplied and controlled mainly by the autonomic nervous system.

In certain embodiments, electrical stimulation of the predetermined area may effectively treat one or more neurological disorder associated with traumatic brain injury (TBI). Physiological conditions associated with TBI that may be treated effectively through electrical stimulation of the C2 and/or C3 dermatome area include, for example, intractable localized, diffuse, or other pain in the head, neck, shoulders, upper extremities, or low back, fibromyalgia chronic syndrome fatigue, or other diffuse pain in one or more regions of the body, or other pain symptoms. Instead or in addition to such physiological conditions, psychological and other conditions associated with TBI that may be treated effectively through electrical stimulation of the C2 and/or C3 dermatome area include, for example, intractable nausea (e.g., from gastroparesis), sleep disorders, sleep apnea, immune-mediated disorders, inflammatory disorders, cardiovascular disorders, improve cardiac function and/or performance, chronic fatigue, behavioral modifications (e.g., lassitude, reduced motivation, depression, emotional distress, irritability, aggression, anxiety, erratic mood swings, personality changes, and loss of enjoyment), sexual dysfunction, and other conditions. Instead or in addition to physiological, psychological, and other conditions such as those described above, conditions associated with TBI that may be treated effectively through electrical stimulation of the C2 and/or C3 dermatome area include decreased cognitive functioning in the form of, for example, impaired memory (e.g., short-term memory, visual memory, and auditory memory), reduced attention and concentration, and reduced information processing capacity (e.g., learning capacity, ability to process complex information, ability to operate simultaneously on different information, ability to rapidly shift attention, ability to plan and sequence, visuomotor capability, auditory language comprehension, and verbal fluency).

In certain embodiments, qEEG analysis may be performed before and after electrical stimulation to determine whether and the extent to which changes in the brain and associated improvements in cognitive functioning effected during electrical stimulation persist after electrical stimulation ceases and for how long. In certain embodiments, the electrical stimulation may modify the brain such that the qEEG is shifted towards normal, as reflected in a normative reference database for example, or otherwise influenced in a positive manner. In other embodiments, it is envisioned that the qEEG and electrode stimulating device may be an all in one type system.

In certain embodiments, one or more appropriate neuropsychological measures may also be used to assess the short term and long term impact of treatment. Observations of improved cognitive function in persons treated according to the present invention suggest that electrical stimulation of the C2 and/or C3 dermatome area may provide a level of cortical stimulation sufficient to maintain cognitive gains even after electrical stimulation ceases.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 3A-3B illustrate examples of the C2 dermatome area; FIG. 3A-1 and FIG. 3A-2 show the cervical dermatomes, including C2 and C3 dermatome. FIG. 3B shows the anatomy of the occiput or occipital area of a subject's head. Anatomical structures shown include nerves, muscle and the galea.

FIGS. 5A-5B show the relative power QEEG recordings without stimulation (A) and with stimulation (B).

FIGS. 6A-6B show the results from the Thatcher Discriminate Analyses without stimulation (A) and with stimulation (B).

FIG. 11A shows the result from a trial stimulation period and FIG. 11B shows the results after implantation into the stimulation system into the C2 dermatome area.

DETAILED DESCRIPTION OF THE INVENTION

I. Definitions

Figure 1A:
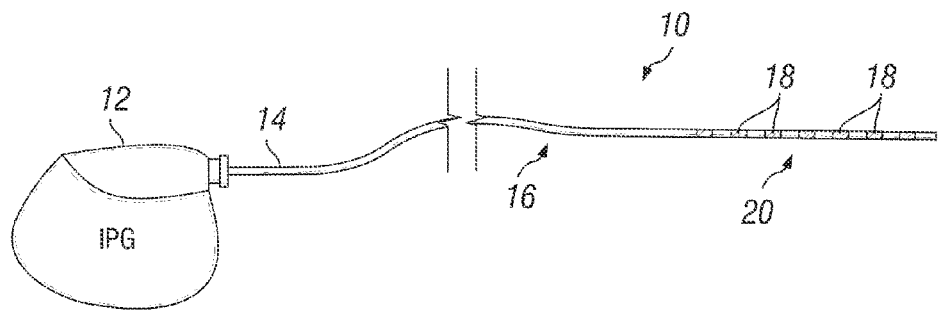
FIGS. 1A-1B illustrate example neurological stimulation systems for electrically stimulating peripheral nerves or neuronal tissue to treat one or more neurological disorders or conditions.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein the term "affective disorders" refers to a group of disorders that are commonly associated with co-morbidity of depression and anxiety symptoms.

As used herein the term "anxiety" refers to an uncomfortable and unjustified sense of apprehension that may be diffuse and unfocused and is often accompanied by physiological symptoms.

As used herein the term "anxiety disorder" refers to or connotes significant distress and dysfunction due to feelings of apprehension, guilt, fear, etc. Anxiety disorders include, but are not limited to panic disorders, posttraumatic stress disorder, obsessive-compulsive disorder and phobic disorders.

As used herein, the term "cardiovascular disease or disorder" refers to disease and disorders related to the cardiovascular or circulatory system. Cardiovascular disease and/or disorders include, but are not limited to, diseases and/or disorders of the pericardium (i.e., pericardium), heart valves (i.e., incompetent valves, stenosed valves, Rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids).

As used herein, the term "depression" refers to a morbid sadness, dejection, or melancholy.

As used herein, the term "dementia" refers to the loss, of cognitive and intellectual functions without impairment of perception or consciousness. Dementia is typically characterized by disorientation, impaired memory, judgment, and intellect, and a shallow labile affect.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. The predetermined site selected from the group consisting of C2 dermatome area, C3 dermatome area, cervical nerve roots (e.g., C1, C2, C3, C4, C5, C6, C7 and C8) and cranial nerves (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve).

As used herein, the term "dermatome" refers to the area of skin innervated by a single dorsal root. One of skill in the art realizes that the boundaries of dermatomes are not distinct and in fact overlap because of overlapping innervations by adjacent dorsal roots. Dermatomes are divided into sacral (S), lumbar (L), thoracic (T) and cervical (C). Yet further, as used herein, the term "dermatome" includes all the neuronal tissues located within the region or adjacent the dermatome area, for example, it may include any peripheral nerve, for example, any cervical nerve root (C1, C2, C3, C4, C5, C6, C7 and C8) that may innervate the dermatome, any and cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) that may innervate the dermatome. Thus, while to some, dermatomes may have a meaning that relates specifically to sensory neurons, as used herein, this limitation should not be applied, but rather the broader description used herein should be used.

As used herein, the term "C2 dermatome area" refers to the area or the dermatome that covers the occiput or occipital area and the top portion of the neck. Yet further, C2 dermatome area includes the neuronal tissue that is located within this area, for example, the C2 dermatome area and its branches innervate the C2 dermatome, as well as any cervical nerve root and/or cranial nerve that may innervate this area. Thus, the C2 dermatome area may also be referred to as the occiput or occipital area, which refers to the back of the head.

As used herein the term "modulate" refers to the ability to regulate positively or negatively neuronal activity. Thus, the term modulate can be used to refer to an increase, decrease, masking, altering, overriding or restoring neuronal activity. Modulation of neuronal activity affects neurological disorders or conditions of a subject.

As used herein, the term "neuronal" refers to a neuron which is a morphologic and functional unit of the brain, spinal column, and peripheral nerves.

As used herein, the term "neurology" or "neurological" refers to conditions, disorders, and/or diseases that are associated with the nervous system. The nervous system comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be separated anatomically, but functionally they are interconnected and interactive. Yet further, the peripheral nervous system is divided into the autonomic system (parasympathetic and sympathetic), the somatic system and the enteric system. Thus, any condition, disorder and/or disease that effects any component or aspect of the nervous system (either central or peripheral) is referred to as a neurological condition, disorder and/or disease. As used herein, the term "neurological" or "neurology" encompasses the terms "neuropsychiatric" or "neuropsychiatry" and "neuropsychological" or "neuropsychological". Thus, a neurological disease, condition, or disorder includes, but is not limited to cognitive disorders, affective disorders, movement disorders, mental disorders, pain disorders, sleep disorders, etc.

As used herein, the term "neuropsychiatry" or "neuropsychiatric" refers to conditions, disorders and/or diseases that relate to both organic and psychic disorders of the nervous system.

As used herein, the term "neuropsychological" or "neuropsychologic" refers to conditions, disorders and/or disease that relate to the functioning of the brain and the cognitive processors or behavior.

The term "overweight" as used herein refers to an excess of body weight compared to standards height/weight tables that are known and used in the art. The excess weight may be from muscle, bone, fat, and/or body weight.

The term "obese" or "obesity" as used herein refers to having an abnormally high proportion of body fat. A body weight 20% over that in standard height-weight tables is arbitrarily considered obesity. Obesity may be classified as mild (20 to 40% overweight), moderate (41 to 100% overweight), or severe (>100% overweight). Obesity is a condition in which there is an excess of body fat. Obesity can be defined as a subject having at least a 20 percent or greater increase over desirable relative weight. A more accurate and operational definition of obesity is based on the Body Mass Index (BMI), which is; calculated as body weight per height in meters squared ($kg/m^2$). "Obesity" refers to a condition whereby an otherwise healthy subject has a Body Mass Index (BMI) greater than or equal to 27 $kg/m^2$, or a condition whereby a subject with at least one obesity-related disease has a BMI greater than or equal to 27 $kg/m^2$. A BMI of about 27 $kg/m^2$ is considered to be in the 85th percentile for BMI. Thus, obesity can also be defined as a subject that is greater than or equal to the 85$^{th}$ percentile for BMI. An "obese subject" is an otherwise healthy subject with a Body Mass Index (BMI) greater than or equal to 30 $kg/m^2$ or a subject with at least one obesity-related disease with a BMI greater than or equal to 27 $kg/m^2$.

As used herein, the term "stimulate" or "stimulation" refers to electrical and/or magnetic stimulation that modulates the predetermined sites in the brain.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Electrical Stimulation Devices

Figure 1B:
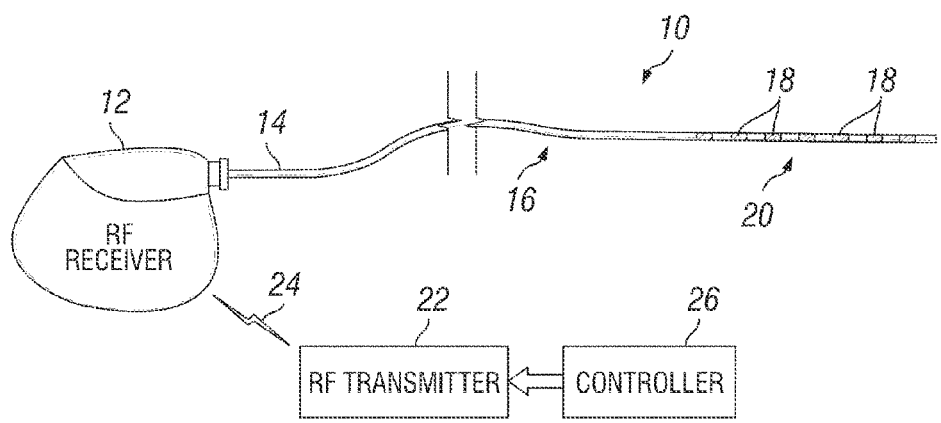
Figure 2A:
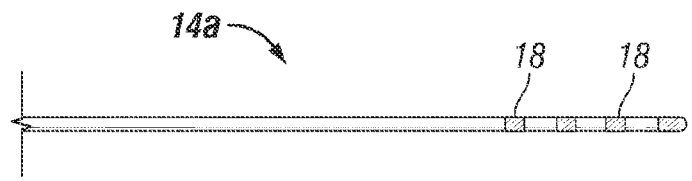
FIGS. 2A-2I illustrate example electrical stimulation leads that may be used to electrically stimulate the peripheral nerves or neuronal tissue to treat one or more neurological disorders or conditions.
Figure 2B:
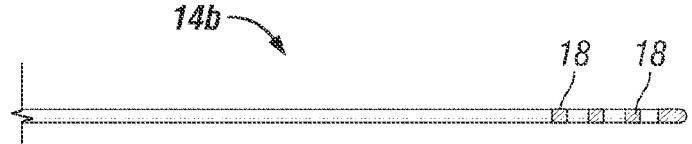
Figure 2C:
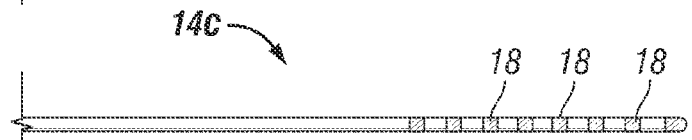
Figure 2D:
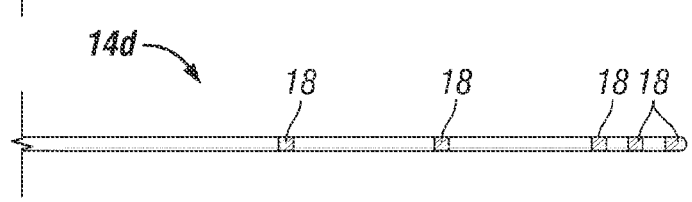
Figure 2E:
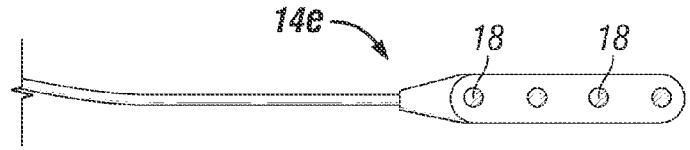
Figure 2F:
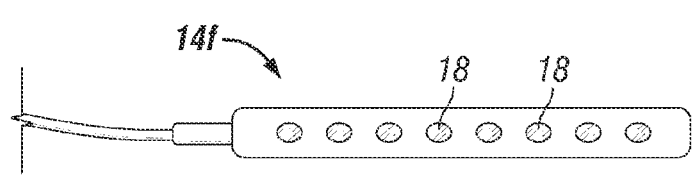
Figure 2G:
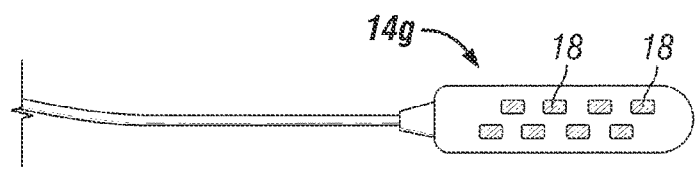
Figure 2H:
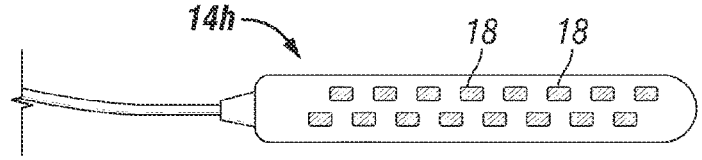
Figure 2I:
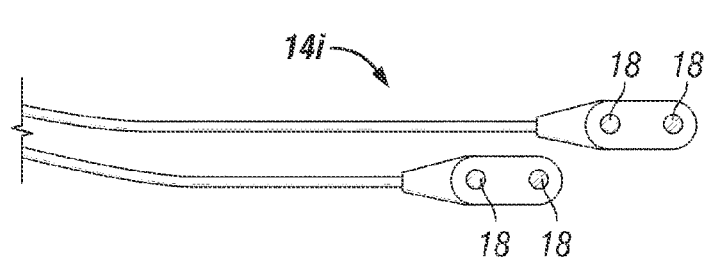

FIGS. 1A-1B illustrate example neurological stimulation systems 10 for electrically stimulating a predetermined site area to treat one or more neurological disorders or conditions. In general terms, stimulation system 10 includes an implantable pulse generating source or electrical stimulation source 12 and one or more implantable electrodes or electrical stimulation leads 14 for applying electrical stimulation pulses to the a predetermined site. In operation, both of these primary components are implanted in the person's body, as discussed below. In certain embodiments, stimulation source 12 is coupled directly to a connecting portion 16 of stimulation lead 14. In certain other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site to stimulate peripheral nerves, according to suitable stimulation parameters (e.g., duration, amplitude or intensity, frequency, pulse width, etc.). The predetermined site is selected from the group consisting of C2 dermatome area, C3 dermatome area, cervical nerve roots (e.g., C1, C2, C3, C4, C5, C6, C7 and C8) and cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and the hypoglossal nerve). A doctor, the patient, or another user of stimulation source 12 may directly or indirectly input stimulation parameters to specify or modify the nature of the stimulation provided.

In one embodiment, as shown in FIG. 1A, stimulation source 12 includes an implantable pulse generator (IPG). An example IPG may be one incorporated in the Genesis® System manufactured by Advanced Neuromodulation Systems, Inc., part numbers 3604, 3608, 3609, and 3644. In another embodiment, as shown in FIG. 1B, stimulation source 12 may include an implantable wireless receiver. An example wireless receiver may be one incorporated in the Renew® System manufactured by Advanced Neuromodulation Systems, Inc., part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the stimulation parameters of stimulation pulses transmitted through stimulation lead 14 to the C2 dermatome area. Thus, the external controller 26 can be for example, a handheld programmer, to provide a means for programming the IPG. An example wireless transmitter 22 may be one incorporated in the Renew® System manufactured by Advanced Neuromodulation Systems, Inc., part numbers 3508 and 3516.

FIGS. 2A-2I illustrate example stimulation leads 14 that may be used for electrically stimulating the predetermined site to treat one or more neurological disorders. As described above, each of the one or more stimulation leads 14 incorporated in stimulation system 10 includes one or more stimulation electrodes 18 adapted to be positioned in communication with the predetermined site and used to deliver to the stimulation pulses received from stimulation source 12. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous", electrical nerve stimulation (TENS) the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

In certain embodiments, the stimulation may be continuous or administered as needed. In other embodiment, the stimulation is randomly generated in order to modulate effects such as nerve plasticity.

It is envisaged that the patient will require intermittent assessment with regard to patterns of stimulation. Different electrodes on the lead can be selected by suitable computer programming, such as that described in U.S. Pat. No. 5,938, 690, which is incorporated by reference here in full. Utilizing such a program allows an optimal stimulation pattern to be obtained at minimal voltages. This ensures a longer battery life for the implanted systems.

III. Implantation of Electrical Devices

Figure 3B:
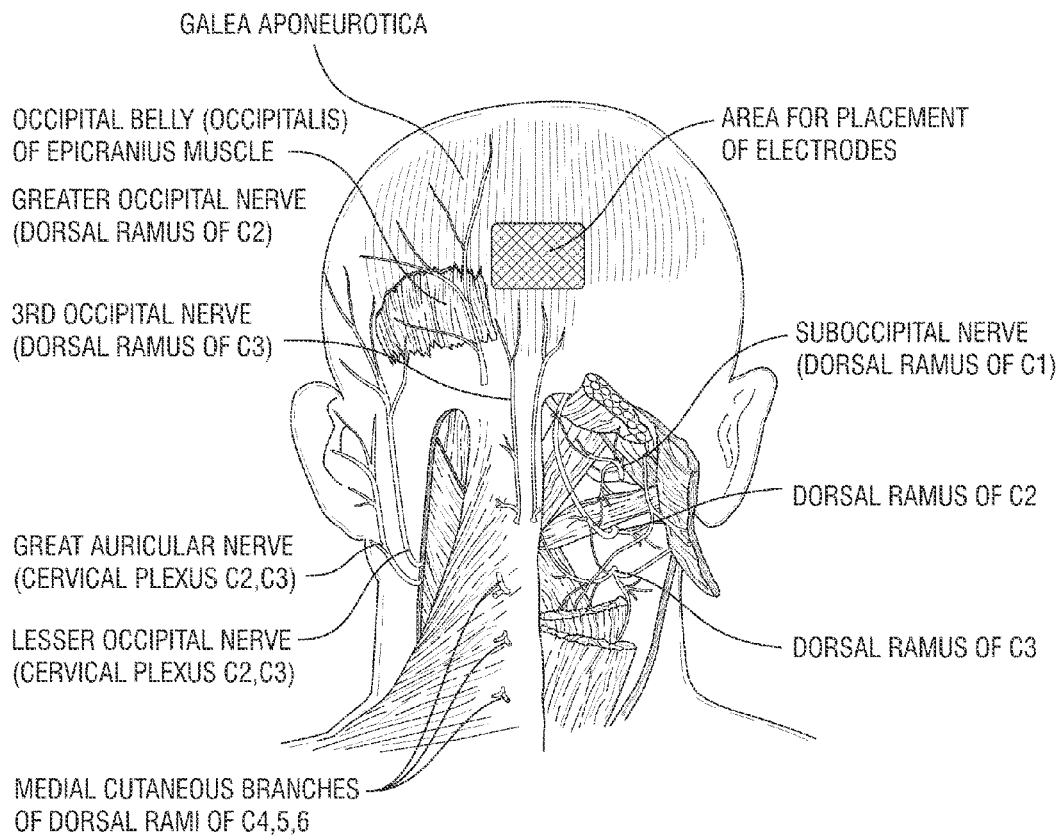
Figures 1, 2, 3, 5A:
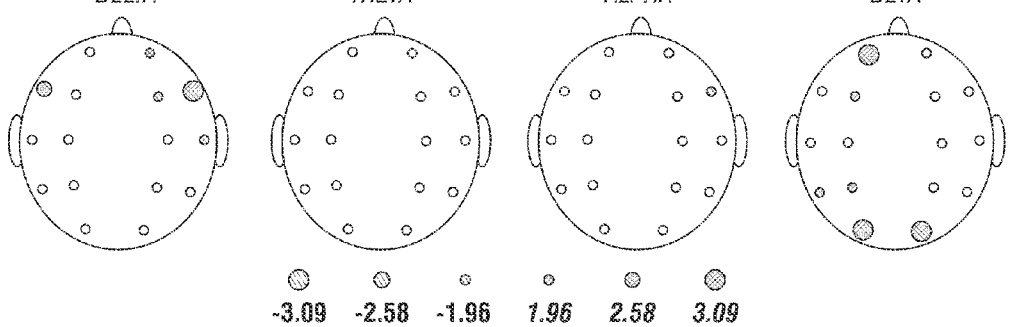

FIGS. 3A-3B illustrate examples of one or more stimulation leads 14 implanted subcutaneously such that one or more stimulation electrodes 18 of each stimulation lead 14 are positioned in communication with the C2 dermatome area, C3 dermatome area, cervical nerve roots (e.g., C1, C2, C3, C4, C5, C6, C7 and C8) cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and hypoglossal nerve) and/or occipital area FIGS. 3A-1 and 3A-2 illustrate example placement of a single stimulation lead 14 for medial electrical stimulation of the C2/C3 dermatome area. In certain embodiments one or more stimulation electrodes 18 are positioned in the C2 dermatome area, subcutaneously, but superior to the galea. Within certain areas of the C2 dermatome area, there is little or no muscle, this area primarily consists of fat, fascia, perostium, and neurovascular structures (e.g., galea), as shown in FIG. 3B. Thus, the advantage implanting a stimulation lead in this area is that there will be no to little muscular contraction. One of skill in the art is aware that stimulation of the C2 dermatome area may result in stimulation of various neuronal structures, for example, but not limited to the C2 dermatome area, C3 dermatome, cranial nerves or other cervical nerve roots.

Figure 4:
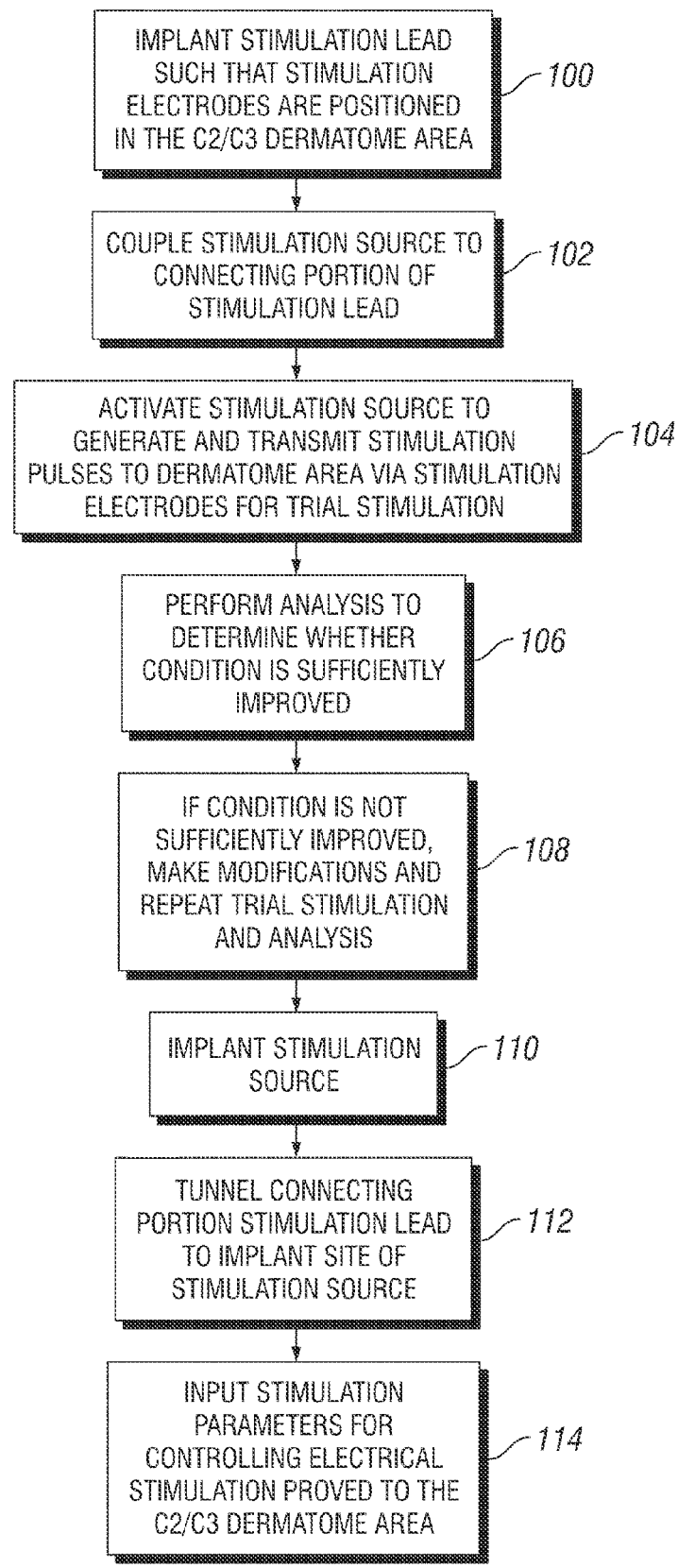
FIG. 4 illustrates an example method of implanting the neurological stimulation system of FIGS. 1A-1B into a person's body for electrical stimulation of a peripheral nerve to treat one or more neurological disorders or conditions.

FIG. 4 illustrates an example method of implanting stimulation system 10, described above, into a person's body with stimulation lead 14 located in communication with a C2/C3 dermatome area for electrical stimulation to treat a neurological disorder or condition. At step 100, one or more stimulation leads 14 are implanted such that one or more stimulation electrodes 18 of each stimulation lead 14 are positioned within the C2/C3 dermatome area (for the purposes described herein and as those skilled in the art will recognize, when an embedded stimulation system, such as the Bion®, is used, it is positioned similar to positioning the lead 14). Techniques for implanting stimulation leads such as stimulation lead 14 are known to those skilled in the art. In certain embodiments, as described above, one or more stimulation electrodes 18 are positioned in communication with the neuronal tissue of the C2/C3 dermatome area. At step 102, if necessary, stimulation source 12 may be coupled directly to connecting portion 16 of stimulation lead 14. Alternatively, as described above and if necessary, stimulation source 12 may not be coupled directly to stimulation lead 14 and may instead be coupled to stimulation lead 14 via an appropriate wireless link. Of course, as those skilled in the art know, an embedded stimulation system will not need to be so coupled.

Intra-implantation trial stimulation may be conducted at steps 104 through 108. Alternatively, the method may proceed from step 102 to 110. At step 104, stimulation source 12 is activated to generate and transmit stimulation pulses via one or more stimulation electrodes 18. At step 106, informal subjective questioning of the person, formal subjective testing and analysis according to one or more neuropsychological test batteries, objective qEEG processing and analysis, or other analysis may be performed to determine whether the one or more neurological disorder, or other conditions are sufficiently improved through the intra-implantation trial stimulation. If the one or more neurological, or other conditions are not sufficiently improved, one or more stimulation parameters may be adjusted, stimulation lead 14 may be moved incrementally or even re-implanted, or both of these modifications may be made at step 108 and the trial stimulation and analysis repeated until the one or more neurological conditions are sufficiently improved. Once the stimulation parameters have been properly set and stimulation lead 14 has been properly positioned such that the one or more physiological, psychological, or other conditions are sufficiently improved, intra-implantation trial stimulation is complete.

Once stimulation lead 14 has been properly implanted and secured, and any trial stimulation completed, if necessary, stimulation source 12 is implanted at step 110. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the upper chest or buttocks. Where stimulation lead 14 includes connecting portion 16, connecting portion 16 may be tunneled, at least in part, subcutaneously to the implant site of stimulation source 12 at step 112. At step 114, a doctor, the patient, or another user of stimulation source 12 may directly or indirectly input stimulation parameters for controlling the nature of the electrical stimulation provided to the C2 dermatome area, if not already set during any intra-implantation trial stimulation period. Where appropriate, post-implantation trial stimulation may be conducted, over one or more weeks or months for example, and any necessary modifications made accordingly. For example, in addition to qualitative analysis of the effectiveness of treatment, where a person's qEEG prior to treatment was abnormal, qEEG analysis may be performed to determine whether and the extent to which electrical stimulation of the C2/C3 dermatome area has shifted the person's qEEG towards normal, as reflected in a normative reference database for example, or otherwise influenced the person's qEEG in a positive manner.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting stimulation system 10 into a person for electrical stimulation of the a predetermined site, such as C2/C3 dermatome area or occipital area to treat one or more neurological disorders or conditions.

IV. Treatment of Neurological Conditions, Disorders, or Diseases

The present method acts to stimulate nerve afferents which in turn stimulate the brain and cause/allow the brain to act in the best interest of the host through use of the brain's natural mechanisms. The prior art fails to recognize that stimulation of at least one of a patient's nerves located in the C2 dermatome area or occipital area can provide the therapeutic treatments according to the instant invention. In addition to the C2 dermatome area, the present invention may also stimulate the C3 dermatome area, cervical nerve roots (e.g., C1, C2, C3, C4, C5, C6, C7 and C8) and cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and hypoglossal nerve) to provide therapeutic treatments according to the instant invention.

It may come as a surprise to one skilled in the art to learn that stimulation of at least one of a patient's nerves located in or associated with the C2/C3 dermatome area or occipital area may be used to treat the maladies disclosed herein. While the normal functions of the nerves associated with the C2/C3 dermatome area or occipital area would not suggest to one skilled in the art that they could be used to treat, for example, depression, anxiety, cognitive disorders, compulsive disorders, or other neurological disorders disclosed herein, the nerves associated with the C2/C3 dermatome area or occipital area have qualities which make them suited for the method of the invention.

Accordingly, the present invention relates to modulation of neuronal activity to affect neurological, neuropsychological or neuropsychiatric activity. The present invention finds particular application in the modulation of neuronal function or processing to effect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response.

In certain embodiments, neurological disorders or conditions that can be treated using the present invention include, for example, but are not limited to Developmental Disabilities [e.g., Cerebral Palsy, Mental Retardation, Attention Deficit Disorder (ADD), Pervasive Developmental Disorders and Autistic Spectrum Disorders (e.g., autism and Asperger's disorder), Learning Disabilities (e.g., dyslexia, disorders of motor functions (e.g., dysgraphia, dyspraxia, clumsiness), and nonverbal learning disabilities (e.g., dyscalculia, visuospatial dysfunction, socioemotional disabilities, and ADHD)]; Demyleinating Diseases [e.g., Multiple Sclerosis]; delirium and dementia [e.g., vascular dementia, dementia due to Parkinson's disease, dementia due to HIV disease, dementia due to Huntington's disease, and dementia due to Creutzfeld-Jakob disease; Alzheimer's dementia, multi-infarct dementia, stroke]; affective disorder [e.g., depression, mania, mood disorder, major depressive disorder, bipolar]; movement disorders [e.g, restless leg syndrome, Dyskinesia (e.g., tremor, dystonia, chorea and ballism, tic syndromes (e.g., Tourette's Syndrome), myoclonus, drug-induced movement disorders, Wilson's Disease, Paroxysmal Dyskinesias, Stiff Man Syndrome) and Akinetic-Ridgid Syndromes and Parkinsonism]; ataxic disorders [e.g., disturbances of gait]; substance abuse related disorders [e.g., alcohol use disorders, amphetamine use disorders, cannabis use disorders, caffeine induced disorders, cocaine use disorders, inhalant use disorders, opioid use disorders, hallucinogen disorders, sedative, hypnotic, or anxiolytic use disorders, and polysubstance use disorders]; sexual dysfunctions [e.g., sexual arousal disorder, male erectile disorder, female dyspareunia, male hypoactive disorder, and female hypoactive disorder]; eating disorders [e.g., overeating disorder, bulimia nervosa, and anorexia nervosa]; obesity; anxiety and obsessive compulsive disorder syndromes [e.g., anxiety, panic attacks, post-traumatic stress disorder, agoraphobia, obsessive and compulsive behavior]; impulse control disorders (e.g., pathological gambling, intermittent explosive disorder, kleptomania, and pyromania); personality disorders (e.g., schizoid personality disorder, paranoid personality disorder, schizotypal personality disorder, borderline personality disorder, narcissistic personality disorder, histrionic personality disorder, obsessive compulsive personality disorder, avoidant personality disorder, dependent personality disorder, and anti-social personality disorder); and other psychiatric disorders [e.g., schizophrenia subtypes, schizoaffective disorder, schizophrenia undifferentiated, delusional disorder, cyclothymic disorder, somatoform disorder, hypochondriasis, dissociative disorder, and depersonalization disorder]; and Chiari I malformation.

In further embodiments, it is contemplated that stimulation of the C2/C3 dermatome area or occipital area modulates gastric motility. In certain embodiments of the invention, esophageal, stomach, small intestinal, and/or large intestinal motility is altered. The gastrointestinal disorders or conditions contemplated by the present invention include gastrointestinal altered motility, sensitivity and secretion disorders in which one or more of the symptoms and conditions affect the gastrointestinal tract from the mouth to the anus. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, menstrual cramps, pancreatitis, spastic and interstitial cystitis and ulcers and the visceral pain associated therewith. One with skill in the art is aware that any functional gastrointestinal disorder, including but not limited to those associated with gastric motility, is appropriate for treatment with the method and systems of the present invention.

The present invention is also appropriate for treating a variety of eating disorders and conditions, including obesity, anorexia nervosa, and bulimia nervosa. For example, it is contemplated that the method of the present invention may be used to treat patient for obesity, binge eating, or compulsive overeating. A stimulator as described herein can be implanted in the patient. The stimulator may be turned "on," thus activating the electrical stimulation to the appropriate nervous tissue associated with a thoracic vertebral segment, by the patient when feelings of hunger are present. Alternatively, it is contemplated that the patient may use the stimulation in a continuous manner.

Yet further other conditions that can be treated include immune-diseases. Immune-mediated diseases include, for example, but not limited to, arthritis (e.g., rheumatoid arthritis and psoriatic arthritis), inflammatory bowel diseases (e.g., ulcerative colitis and Crohn's disease), endocrinopathies (e.g., type 1 diabetes and Graves disease), neurodegenerative diseases (e.g., multiple sclerosis, autistic spectrum disorder, Alzheimer's disease, Guillain-Barre syndrome, obsessive-compulsive disorder, optic neuritis, retinal degeneration, amyotrophic lateral sclerosis (ALS), Parkinson's disease, Huntington's Disease, Guillain-Barre syndrome, myasthenia gravis, and chronic idiopathic demyelinating disease (CID)), vascular diseases (e.g., autoimmune hearing loss, systemic vasculitis, and atherosclerosis), and skin diseases (e.g., dermatomyositis, systemic lupus erthematosus, discoid lupus erthematosus, scleroderma, and vasculitics).

In certain aspects of the present invention, the stimulation system can be used to treat neuroendocrine disorders, such as disorders associated with the crosstalk that occurs between the endocrine system and the nervous system. More particularly, the stimulation system of the present invention can be used to treat disorders associated with the hypothalamic-pituitary-adrenal (HPA) and -gonadal (HPG) axes, as well as disorders associated with the autonomic nervous system. Diseases associated with the HPA axis can include, but are not limited to pituitary tumors, Cushing syndrome, adrenal insufficiency, ACTH resistance, Congenital Adrenal Hyperplasia (CAH), adrenocortical tumors, glucocorticoid resistance/hypersensitivity, and mineralocorticoid resistance. Diseases of the HPG axis can include, but are not limited to hypothalamic hypogonadism, disturbances of the menstrual cycle, ovarian and testicular gonadotropin resistance, endometriosis, and infertility. Disease associated with the autonomic nervous system can include, but are not limited to pheochromocytoma and catecholamine deficiency. Still further, developmental/psychiatric, metabolic and immune disorders related to the functions of the HPA and HPG axes and the autonomic system can include, but are not limited to premature adrenarche, eating disorders,—including anorexia and bulimia nervosa and adolescent obesity—,adolescent conduct disorder, dysthymia and depression, childhood asthma and rheumatoid arthritis, the premenstrual tension syndrome, and postpartum and climacteric depression and autoimmunity. In certain embodiments of the present invention, the subject may increase the stimulation during the day and decrease the stimulation during the night or evening. This type of cyclic alteration or variation in the stimulation parameters may effect the circadian rhythm of the subject thereby altering cortisol production and/or release from the HPA.

Still further, the stimulation system of the present invention can be used to provide stimulation to the predetermined sited to enhance or improve cardiac function, for example, hemodynamics, electrical activity (e.g., stabilize and/or regulate heart rate), myocontractility, perfusion of the heart muscle, perfusion of the entire body, as well as enhancement cardiac performance or efficiency, such as balance between supply and demand. Thus, the present invention can be used as a prophylactic system to enhance or improve cardiac function.

In further embodiments, improvement of cardiac function may be necessary after a heart attack and/or myocardial infarction, thus the present invention can be used to decrease and/or lessen and/or alleviate damage suffered from the heart attack or myocardial infarction. Still further, the present invention may be used in conjunction with cardiovascular surgical procedures to improve and/or enhance cardiac function such surgical procedures may include, but are not limited to coronary artery bypass graft (CABG), angioplasty, cardiovascular stent, cardiac catheterization procedures, heart valve repairs and/or replacements, heart transplants, great vessel repair, ablations or other electrophysiological procedures. Thus, the present invention can be used for a therapeutic system to improve cardiac function.

In addition to being used as a prophylactic system to enhance or improve cardiac function and/or performance. The present invention may be used to as a therapeutic system to treat cardiovascular disorders, such as heart failure, ventricular tachycardia, supraventricular tachycardia, ischemia (e.g., cardiac and/or vascular), arrhythmias, perfusion imbalances (e.g., cardiac perfusion and/or vascular perfusion) imbalance of autonomic tone, or the like. Those of skill in the art recognize that imbalances in vascular perfusion may result in a stroke, thus, the present invention may be used to reduce the damage, prevent and/or reduce the risk of a stroke in a subject.

The present invention can also be used for other symptoms that can be related cardiovascular diseases include cholesterol and/or blood pressure. Thus, the present invention can be used to decrease cholesterol levels and/or to regulate blood pressure, for example decrease blood pressure in a subject suffering from high blood pressure and/or decrease cholesterol levels in a subject suffering from high cholesterol. In addition to regulating blood pressure, the stimulation system of the present invention may also alleviate or lessen hot flashes.

In specific embodiments, the cardiovascular disease is atherosclerosis. Prophylactic treatment can be administered to those subjects at risk for developing atherosclerosis. One risk factor is an atherogenic lipoprotein profile. For example, a ratio of serum cholesterol to high density lipoproteins of above 5:1 indicates a higher than average risk of developing atherosclerosis. Other factors indicating increased risk for atherosclerosis include a serum cholesterol level of above 240 mg/dl; a high density lipoprotein level below about 35 mg/dl; and a low density lipoprotein level above about 160 mg/dl.

Another embodiment includes treating a human subject with an elevated level of circulating total cholesterol according to the then medically established guidelines. It is contemplated that the stimulation system of the present invention reduces or attenuates the levels of circulating total cholesterol, low density lipoproteins or very low density lipoproteins.

Yet further, the stimulation system of the present invention can be use to provide stimulation to the predetermined site to modulate blood glucose. Blood glucose can be used as an indicator of diabetes mellitus. Thus, it is envisioned that the present invention may be used to treat diabetes mellitus. Diabetes mellitus is non-insulin dependent diabetes mellitus or insulin dependent diabetes mellitus. The symptoms of diabetes mellitus can be selected from the group consisting of obesity, hyperglycemia, and increased insulin levels. Blood glucose is monitored by the level of glycosylated hemoglobin (HbA1c). Yet further, the present invention may also stabilize hemoglobin levels.

Still further, the stimulation system of the present invention may be used to alleviate sleep disorders. One of skill in the art realizes that as people age, they loose stage 4 of the sleep cycle. Thus, the stimulation system of the present invention can to restore the sleep cycle Other sleep disorders include, but are not limited to sleep apnea.

The present invention finds particular utility in its application to human neurological disorders, for example psychological or psychiatric activity/disorder. One skilled in the art appreciates that the present invention is applicable to other animals which exhibit behavior that is modulated by the neuronal tissue. This may include, for example, primates, canines, felines, horses, elephants, dolphins, etc. Utilizing the various embodiments of the present invention, one skilled in the art may be able to modulate neuronal functional outcome to achieve a desirable result.

One technique that offers the ability to affect neuronal function is the delivery of electrical and/or chemical stimulation for neuromodulation directly to target tissues via an implanted device having a probe. The probe can be stimulation lead or electrode assembly. The electrode assembly may be one electrode, multiple electrodes, or an array of electrodes in or around the target area. The proximal end of the probe is coupled to system to operate the device to stimulate the target site. Thus, the probe is coupled to an electrical signal source, which, in turn, is operated to stimulate the predetermined treatment site.

The predetermined site can be selected from the group consisting of C2 dermatome area, C3 dermatome area, cervical nerve roots (e.g., C1, C2, C3, C4, C5, C6, C7 and C8) and cranial nerves (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve). One of skill in the art realizes that the C2 dermatome area covers the occipial area and the More specifically, the cranial nerves that may be stimulated in the occipital area is the hyoglossal nerve, accessory nerve, the vagal nerve and the facial nerve.

In certain embodiments, the predetermined site is a C2/C3 dermatome area. The advantage of stimulating the C2/C3 dermatome area, which comprises the occiput and the top portion of the neck, comprises skin, fat, fascia, periostium, and neurovascular structures. This area is innervated by the branches of the C2/C3 dermatome area, as well as other cervical nerve roots (e.g., C1, C2 and C3). One of skill in the art is aware that the C2 dermatome area is a peripheral nerve that exits the spinal cord at the C2 level of the cervical vertebrae and extends upward generally along the back and the back-sides of the head. The lesser C2 dermatome area extends upward and toward the sides of the head. The greater C2 dermatome area extends upward toward the top of the head. And the third C2 dermatome area extends from near the neck around the back of the head toward the ear. In certain areas of the C2 dermatome area, there is very little to no muscle structures. Thus, since there is no or very little muscle to result in muscle contraction due to stimulation, the amplitude limits can be considerably higher than if the electrode was implanted in an area comprising muscle.

Using the therapeutic stimulation system of the present invention, the predetermined site or target area is stimulated in an effective amount or effective treatment regimen to decrease, reduce, modulate or abrogate the neurological disorder. Thus, a subject is administered a therapeutically effective stimulation so that the subject has an improvement in the parameters relating to the neurological disorder including subjective measures such as, for example, neurological examinations and neuropsychological tests (e.g., Minnesota Multiphasic Personality Inventory, Beck Depression Inventory, Hamilton Rating Scale for Depression, or Yale-Brown Obsessive Compulsive score (Y-BOCS)), motor examination, and cranial nerve examination, and objective measures including use of additional psychiatric medications, such as anti-depressants, or other alterations in blood flow or metabolism in the brain, alterations in the EEG or qEEG. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment of the present invention, the target site is stimulated using stimulation parameters such as, pulse width of about 5 to about 200 microseconds, more preferable, about 10 to about 100 microseconds; frequency of about 3 to about 30 Hz, more preferably, about 3 to about 10 Hz, more preferably, 4 to about 6 Hz; and amplitude of about 2 to about 100 mA, more preferably about 4 to about 30 mA. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

Clinical observations indicate that the efficacy of treatment may be correlated to the amplitude or intensity; that is, the higher the amplitude or intensity, the more pronounced the therapeutic effect. Also, unlike certain other types of stimulation such as electrical stimulation of the spinal cord to treat pain, with electrical stimulation of the neuronal tissue in the C2/C3 dermatome area it is generally not necessary for the patient to feel the electrical stimulation to experience the therapeutic effect. Many patients cease to feel the electrical stimulation after a time, yet the beneficial effects remain. In such cases, the pain threshold of the patient appears to be elevated globally, as well as locally at the dermatome. When the amplitude or intensity of the electrical stimulation is increased such that the patient can again feel the electrical stimulation, the patient may experience a further amplification of the beneficial effects. After a time (e.g., approximately thirty minutes) being stimulated at the increased amplitude or intensity, the ability of the patient to feel the electrical stimulation again fades. In certain embodiments, this phenomenon may allow the amplitude or intensity to be increased more or less indefinitely to achieve increased beneficial effects. Efficacy may also be correlated with the area to be stimulated. For example, the greater the coverage area or the area that the stimulator covers the greater the efficacy. The area coverage can be in the range of about 30 mm to about 150 mm, more specifically, 50 mm to about 100 mm. Still further, in certain embodiments the stimulation area can include the C2 dermatome that comprises the mid-line to about the ear. One of skill in the art realizes that the electrodes may be bilateral electrodes and implantation of bilateral electrodes does not necessarily require the electrodes to be symmetrical across the mid-line.

The patient can be in control of the stimulation parameters and/or programs to maintain effectiveness of the stimulation system. For example, the patient can change the programs on a periodic basis, for example weekly to maintain effectiveness. Other patients may increase the stimulation during the day and decrease the stimulation parameters during the evening or vice versa.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective.

In certain embodiments, in connection with improvement in one or more of the above or other neurological disorders, the electrical stimulation may have a "brightening" effect on the person such that the person looks better, feels better, moves better, thinks better, and otherwise experiences an overall improvement in quality of life.

In certain embodiments, electrical stimulation of the C2/C3 dermatome area may be provided to effectively treat pain. For example, in certain embodiments, electrical stimulation of the C2/C3 dermatome area may be provided to effectively treat fibromyalgia or other diffuse pain in any one or more regions of the body. The stimulation parameters for treating fibromyalgia may include any suitable range, for example, amplitude in is the range of about 4 to about 20 mA, frequency is in the range of about 4 to about 6 Hz, and the pulse width is in the range of about 20 to about 60 μs. Patients respond to amplitudes in this range, but increases in the amplitudes improve symptoms such that higher amplitudes up to 100 milliamps would be necessary for optimal improvement in more severe cases.

As another example, in certain embodiments, electrical stimulation of the C2/C3 dermatome may be delivered to treat localized, diffuse, or other pain in any one or more regions of the body below the head, such as pain in the neck, shoulders, upper extremities, torso, abdomen, hips, and lower extremities. As another example, in certain embodiments, electrical stimulation of the C2/C3 dermatome may be delivered to treat Reflex Sympathetic Dystrophy (RSD) pain. As another example, in certain embodiments, electrical stimulation of the C2/C3 dermatome area may decrease the person's overall sensitivity to pain or increase the person's overall pain threshold, in certain cases significantly, such that the person experiences "total body" pain relief or other generalized pain relief throughout the body. For example, a person with a relatively low overall pain threshold may experience an elevation of the pain threshold from a relatively hyperalgesic state to a relatively normalized state, with concomitant pain relief throughout the body. Other example pain-related applications of electrical stimulation of the C2/C3 dermatome area in certain embodiments include: (1) treating post-operative pain associated with major surgery, perhaps using a temporary as opposed to a permanent stimulation lead (e.g., to augment or replace opioid analgesia); (2) treating focal pain (e.g., possibly in combination with electrical stimulation of the spinal cord or peripheral structures such as the periostium around the knee or hip); (3) treating pain in elderly patients with severe degenerative spinal or joint conditions (e.g., with additional improvements in sleep, cognition, and mood); and (4) treating trigeminal neuralgia. Yet further, the stimulation system of the present invention may result in pain relief in areas of the head not innervated by the C2/C3 dermatome area (such as outside the C2 dermatome area), for example, but not limited to pain in the face, ears, and mouth. These areas are innervated by the trigeminal nerve and other cranial nerves and those of the cervical plexus.

In certain embodiments, possibly in combination with one or more of the benefits described above, electrical stimulation of the C2/C3 dermatome area may be provided to effectively treat impaired motor functioning. For example, in certain embodiments, electrical stimulation of the C2/C3 dermatome area may be provided to effectively treat lack of coordination in the upper or lower extremities (e.g., gait problems). As another example, in certain embodiments, electrical stimulation of the C2/C3 dermatome area may be provided to effectively treat motor disorders such as tremor (e.g., reducing the coarseness of tremor), dystonia (e.g., reducing the frequency and severity of torticollis or other forms of dystonia), and seizure.

In certain embodiments, electrical stimulation of the C2/C3 dermatome area may effectively treat other conditions including intractable nausea, chronic fatigue, and sleep disorders, for example sleep apnea.

In further embodiments, stimulation of the C2/C3 dermatome area can effectively be used as a treatment for obesity and other eating disorders. Stimulation of the C2/C3 dermatome area can result in the person not sensing hunger or loosing the sense of hunger or loosing the sense or desire to overeat, thereby resulting in weight loss. Thus, a loss of hunger or desire to eat can result in a decrease in caloric intake leading to weight loss. Still further, stimulation of the C2/C3 dermatome area can result in an alteration in the desire for certain food choices. For example, prior to stimulation, the person may desire fattening type food, with stimulation, the person may alter their eating habits such as eating more healthy food, thereby resulting in weight loss.

In certain embodiments, electrical stimulation of the C2/C3 dermatome area may effectively treat one or more neurological disorder associated with traumatic brain injury (TBI). Physiological conditions associated with TBI that may be treated effectively through electrical stimulation of the C2/C3 dermatome area include, for example, intractable localized, diffuse, or other pain in the head, neck, shoulders, upper extremities, or low back, fibromyalgia or other diffuse pain in one or more regions of the body, or other pain symptoms. Instead or in addition to such physiological conditions, psychological and other conditions associated with TBI that may be treated effectively through electrical stimulation of the C2/C3 dermatome area include, for example, intractable nausea (e.g., from gastroparesis), sleep disorders, chronic fatigue, behavioral modifications (e.g., lassitude, reduced motivation, depression, emotional distress, irritability, aggression, anxiety, erratic mood swings, personality changes, and loss of enjoyment), sexual dysfunction, and other conditions. Instead or in addition to physiological, psychological, and other conditions such as those described above, conditions associated with TBI that may be treated effectively through electrical stimulation of the C2/C3 dermatome area include decreased cognitive functioning in the form of, for example, impaired memory (e.g., short-term memory, visual memory, and auditory memory), reduced attention and concentration, and reduced information processing capacity (e.g., learning capacity, ability to process complex information, ability to operate simultaneously on different information, ability to rapidly shift attention, ability to plan and sequence, visuomotor capability, auditory language comprehension, and verbal fluency).

Stimulation parameter that can be used for TBI treatment may include the following ranges, amplitude in the range of about 3 to about 15 mA, frequency in the range of about 4 to about 30 Hz, and the pulse width is about 20 to about 90 microseconds. Of course, one of skill in the art is cognizant that these ranges can be altered to more suitable ranges based upon the particular needs of the subject. Patients respond to amplitudes in this range, but increases in the amplitudes improve symptoms such that higher amplitudes up to 100 milliamps would be necessary for optimal improvement in more severe cases.

As another particular example, in certain embodiments, a preferred range of certain stimulation parameters for treating Chiari I malformation includes an amplitude in the range of about 2 to about 20 mA, a frequency in the range of about 3 to about 7 Hz, and a pulse width in the range of about 20 to about 90 μs. Patients respond to amplitudes in this range, but increases in the amplitudes improve symptoms such that higher amplitudes up to 100 milliamps would be necessary for optimal improvement in more severe cases.

In further embodiments, it is envisioned that the dermatome area may be stimulated in conjugation with cranial nerves, such as the trigeminal nerve, more particularly, V1 of the trigeminal nerve, or any peripheral nerve, such as a peripheral nerve that is located in area comprises little to no contracting tissue, such as muscle.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of TBI

A 38 year old male with traumatic brain injury who suffered from c1/2 fracture, headaches and multifocal pain received an implant in the C2 dermatome area. Prior to stimulation implant, the patient suffered from depression, lack of energy, difficulties in sleeping, attention problems.

Figures 1, 2, 3, 5B:
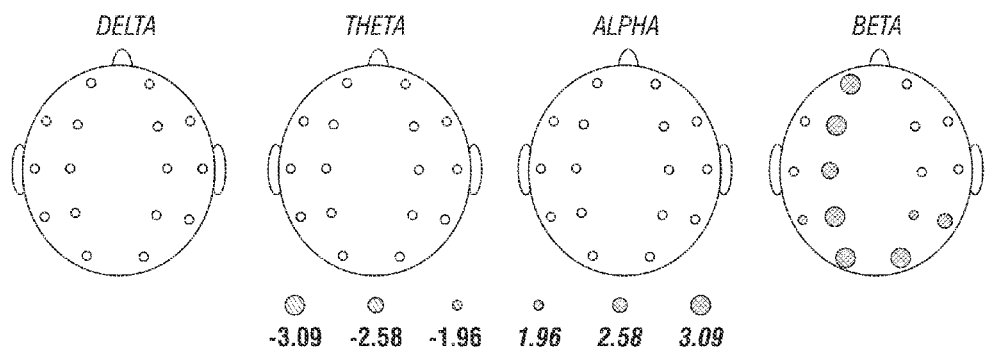

Neuropsychological tests showed about 30% improvement after using the above described invention and QEEG showed a normalization of EEG patterns (See FIG. 5A, 5B).

In addition to the normalization of the EEG patterns, using the above described invention, the patient had marked improvements of his mood and depression and has stopped taking his antidepressants. In addition to an improvement in mood, the patient had improved fine motor control of arms and hands, improvements in sleep, energy level and concentration abilities.

Figure 6B:
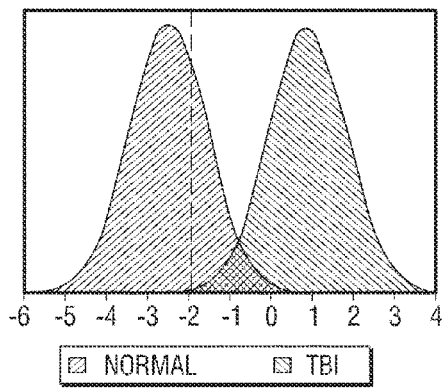

Still further, as shown in FIGS. 6A and 6B, the patient using the above described invention went from a TBI probability index of about 95% to one that was not significant. The TBI probability Index is the subject's probability of membership in the mild traumatic brain injury population (Thatcher et al., EEG and Clin. Neurophysiol., 73:93-106, 1989).

Example 2

Treatment of TBI and RSD

A 33 Year old female with TBI (Traumatic brain injury) and RSD (reflex sympathetic dystrophy of left arm) had symptoms of severe attentional and short term memory impairments, gait problems, anxiety and severe hypersomnolence in which she had to take over 200 mg per day of Ritalin to stay awake. In addition to these neurological conditions, she also suffered from bulemia, as well as severe and chronic constipation in which bowl movements were only about one every 10 days. Yet further, she suffered from nausea and vomiting almost daily.

A stimulation system was implanted in communication with the C2 dermatome using the system and method for the invention as described herein. After the implant, she had complete resolution of RSD pain, and had marked improvement of memory and attentional impairments; improvements in anxiety and improvements in her gait. Hypersomnolence improved to the point where she was able to function on 40 mg per day of Ritalin. QEEG showed a normalization of brain wave activity after implant.

Multiple adjustments in the stimulation parameters on this patient indicated that the best results in all these parameters occurred at frequencies between 4-6 Hz, that narrow pulse widths were better than wide pulse widths, and that a single stimulation set was preferable to multi-stimulation parameter.

Once the stimulations parameters were adjusted, the symptoms of bulemia, for example, self loathing, compulsions to binge eat and purge were ameliorated or lessened.

Example 3

Treatment of TBI, Fibromyalgia and RSD

A 46 year old female with TBI, Fibromyalgia, RSD of leg had symptoms of severe pain in head, neck, shoulders, low back, leg, attentional and memory impairments, chronic fatigue.

A stimulation system was implanted in communication with the C2 dermatome using the system and method for the invention as described herein. After implant she had 100% relief of pain in all areas of the body, and had marked improvements of fatigue, attentional and memory impairment. She was able to read books for pleasure for the first time in many years and could be physically active without pain. Specifically, RSD of the leg and myofascial pain of the neck and trapezius was totally gone. The optimal parameters were a single stimulation set, having frequencies of 4-6 Hz, and narrower pulse widths. This patient also showed that pain thresholds were elevated such that a person who could previously not engage in vigorous physical activity because of hyperalgesia, could now do so and not have an exacerbation of pain.

Thus, these results indicated that C2 dermatome stimulation resulted in improved reading comprehension and attentional deficits, as well as a reduction or treatment of pain in the neck, shoulders, low back, hips, and legs were treatable with this technique.

Example 4

Treatment of TBI and Chiari I Malformation

A 29 year old female with Chiari I malformation suffered severe headaches, fatigue, neck and back pain, attentional and memory impairment.

A stimulation system was implanted in communication with the C2 dermatome using the system and method for the invention as described herein. After implant she had marked improvement of pain and was able to decrease her pain medication over 50%, and had a normalization of memory and attentional problems. No longer had to take naps in the day and could multi-task without problem.

Thus, the results indicated that short term memory impairment was treatable with C2 dermatome stimulation and that multi-tasking impairment was also improved. The optimal parameters were a single stimulation set, having frequencies of 4-6 Hz, and narrower pulse widths. Yet further, the results indicated that "fatigue" or "lack of energy", as a symptom of neurological injury was treatable with C2 dermatome stimulation, as well as symptoms of Chiari I malformation.

Example 5

Treatment of TBI and Agranulocytosis

A 40 year old female suffered from TBI, fibromyalgia, and agranulocytosis for which she took a very potent drug which caused many side effects including headaches and fatigue.

A stimulation system was implanted in communication with the C2 dermatome using the system and method for the invention as described herein. After implant she had a complete resolution of all fibromyalgia pain (previous it had been all over the body) and had a marked improvement in depression such that she could stop all her anti-depressant medication.

Thus, these results showed us that fibromyalgia could be treated with high effectiveness with occipital stimulation, as well as severe migraine headaches.

Example 6

Treatment of TBI and Coma

A 23 year old female suffered a severe head injury at age 13 with about 10 days of a coma. She also suffered from significant attentional and memory impairments as well as intractable pain all over her body, including headaches. The subject was attending college part time and able to obtain grades in the C range.

Figure 7A:
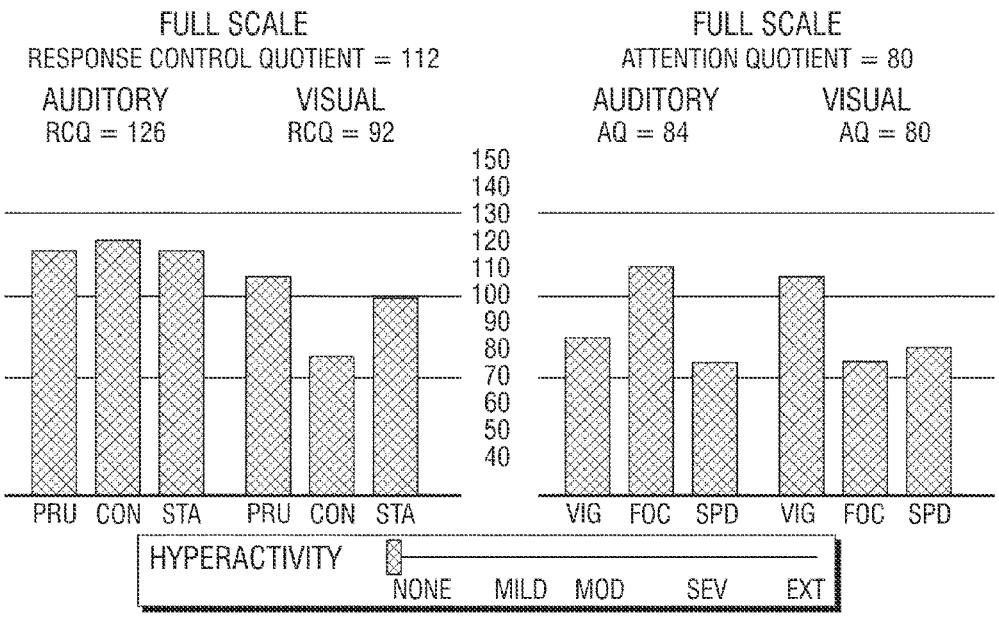
FIGS. 7A-7B show the results of IVA continuous performance without stimulation (A) and with stimulation (B).
Figure 7B:
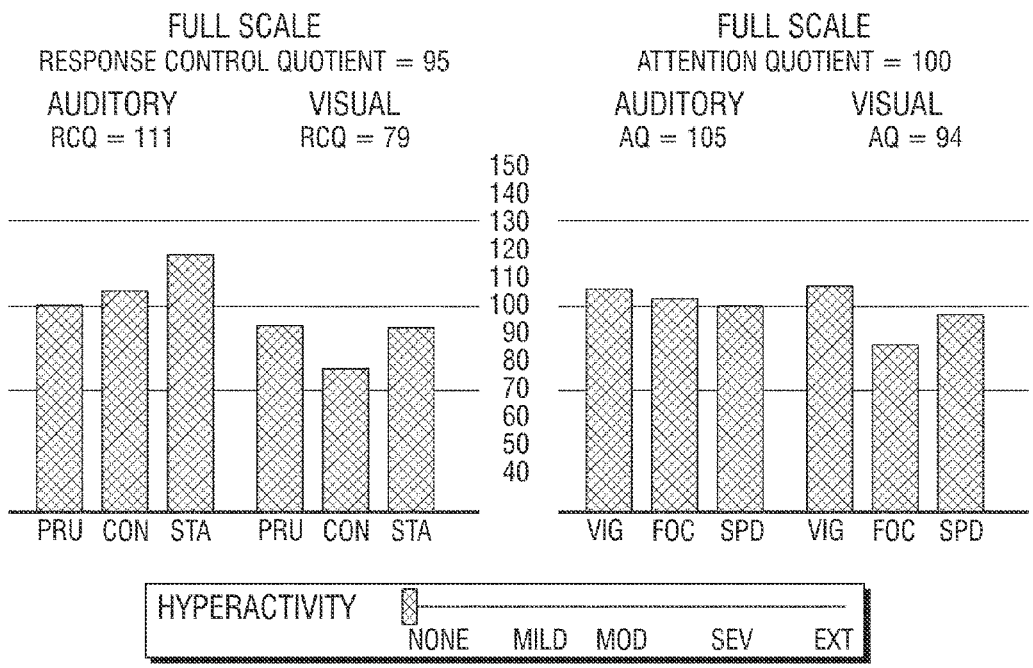

A stimulation system was implanted in communication with the C2 dermatome using the system and method for the invention as described herein. After implant, the subject had a marked improvement in attentional and memory impairments. Neuropsychological testing after implant showed a significant improvement on many measures of visual and auditory processing and attentional tasks measured by IVA Continuous Performance (See FIGS. 7A and 7B). One of skill in the art realizes that a normal IVA is considered is averaged range 90 to 110.

She also had complete resolution of all pain in her body. Still further chronic fatigue was completely gone, as well as her sleep pattern completely restored. QEEG showed a normalization of abnormal brain waves.

Thus, results indicated that all symptoms due to TBI were treated including a myriad of cognitive and attentional problems, and that all pain in the body due to TBI were treated effectively. Yet further, these results indicated that depression was treated by C2 dermatome stimulation.

Example 7

Treatment of TBI and Gait Problems

A 40 year old female suffered from both a brain injury and spinal cord injury spending most of her time in wheelchair. She also suffered from a gait problem, memory and attentional impairments, severe headaches, and severe pain in most areas of the body, as well as severe depression.

A stimulation system was implanted in communication with the C2 dermatome using the system and method for the invention as described herein. After implant her mood was elevated so much that she came off anti-depressants. She had pain relief in all areas of the body except an area of her thoracic spine. She could now walk short distances without a cane and took walks with a cane longer distances. Yet further, she had improvement of cognitive functions, as well as tremor that had been present in her right hand was markedly reduced.

Thus, these results indicated certain types of motor problems such as tremor and gait disturbances due to neurological injury, as well as depression were treated with C2 dermatome stimulation.

Example 8

Treatment of TBI and Chiari I Malformation

A 38 year old female suffered from TBI and Chiari I malformation, as well as pain in her had, neck, and low back, fatigue and attentional deficits.

A stimulation system was implanted in communication with the C2 dermatome using the system and method for the invention as described herein. After implant, pain in her head and neck disappeared, had improved attentional abilities, and had a marked elevation of mood and no anxiety. She scored substantially better on neuropsychological testing post implant.

Thus, these results indicated that symptoms of Chiari I malformation were treated effectively with C2 dermatome stimulation.

Example 9

Treatment of TBI and Gastroparesis

A 33 Year old female suffered from intractable nausea from gastroparesis and co-morbid TBI.

A stimulation system was implanted in communication with the C2 dermatome using the system and method for the invention as described herein. After implant had a 80% reduction in nausea and improvement in pain all over her body.

Thus, these results indicated that that intractable nausea was treated with C2 dermatome stimulation.

Example 10

Treatment of TBI and Depression

A 42 Year old female suffered from with mild TBI, severe depression and anxiety, as well as pain in the neck and arms.

A stimulation system was implanted in communication with the C2 dermatome using the system and method for the invention as described herein. After implant had marked improvement in anxiety and depression, was able to think clearly and interact with her children and spouse much better. She had complete remission of all pain in her neck and upper extremities. Still further, she no longer had to wear splints on her hands.

Figure 8A:
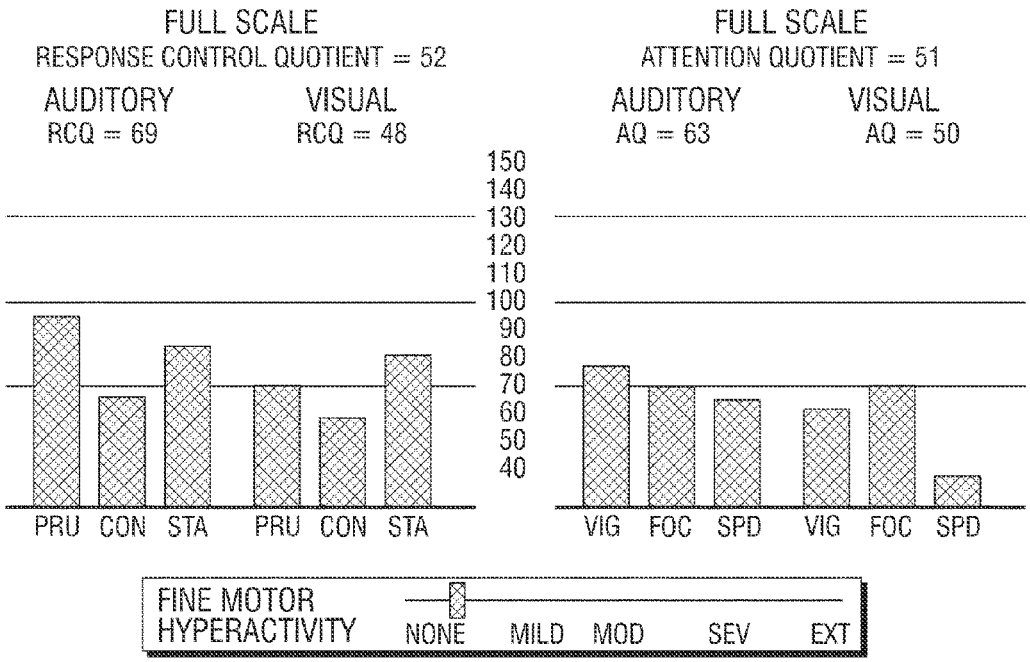
FIGS. 8A-8B show the results of IVA continuous performance without stimulation (A) and with stimulation (B).
Figure 8B:
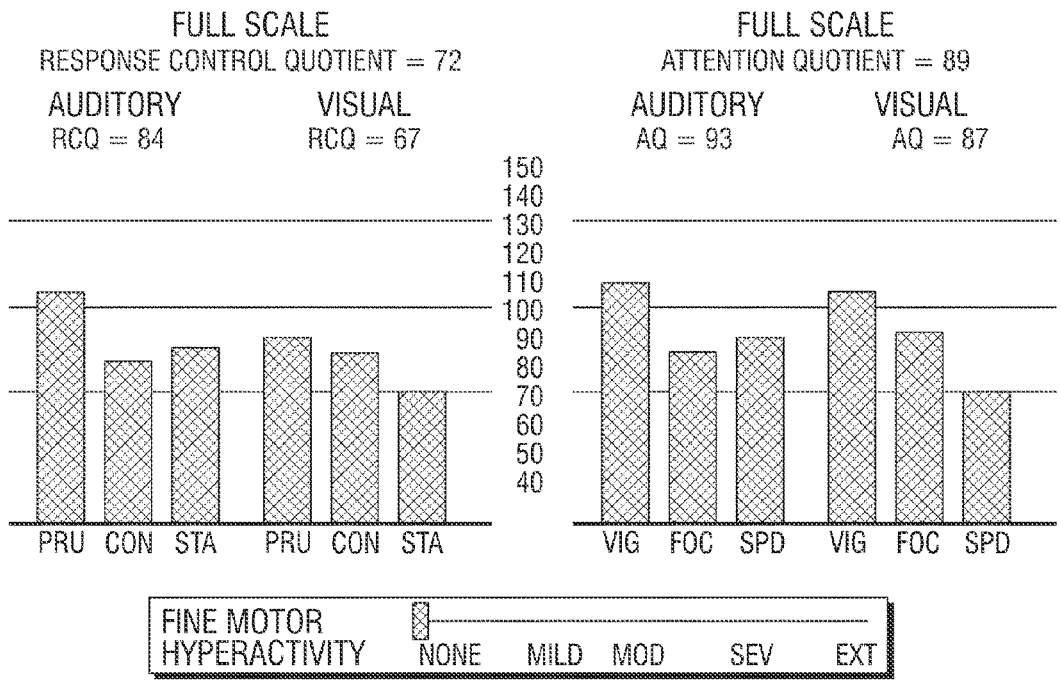

Neuropsychological testing after implant showed a significant improvement on many measures of visual and auditory processing and attentional tasks measured by IVA Continuous Performance (See FIGS. 8A and 8B).

Thus, these results indicated that C2 dermatome stimulation treated cognitive problems associated with TBI, depression, as well as pain relief in the neck, shoulders, and upper extremities.

Example 11

Treatment of TBI, Anxiety and Pain

A 54 year old male suffered from severe neck and low back pain after multiple spinal surgeries. The subject was involved in a care accident in which his pain was markedly elevated.

A stimulation system was implanted in communication with the C2 dermatome using the system and method for the invention as described herein. After implant, he no longer had neck and back pain and could bend and touch his toes without pain for the first time in over 10 years. His mood was markedly improved and he stated that he was always afflicted with severe anxiety. After implant he elected to stop his anti-anxiety medications.

Thus, these results indicated that C2 dermatome stimulation treated low back and neck pain could be effectively treated, as well as anxiety disorders.

Example 12

Treatment of TBI and RSD

A 35 year old female suffered from TBI and RSD all over her body. The symptoms included severe sensitivity to light and sound and constant severe headaches. She could not leave her house without ear plugs or dark glasses.

A stimulation system was implanted in communication with the C2 dermatome using the system and method for the invention as described herein. After implant no longer suffered from hypersensitivity and no longer had to wear dark glasses or ear plugs. Still further, she had improvement in pain all over her body and her pain thresholds, which were very low pre-implant, were now normalized all over her body. She also had improvement in fatigue, attention, concentration, mood, and memory.

Figure 9A:
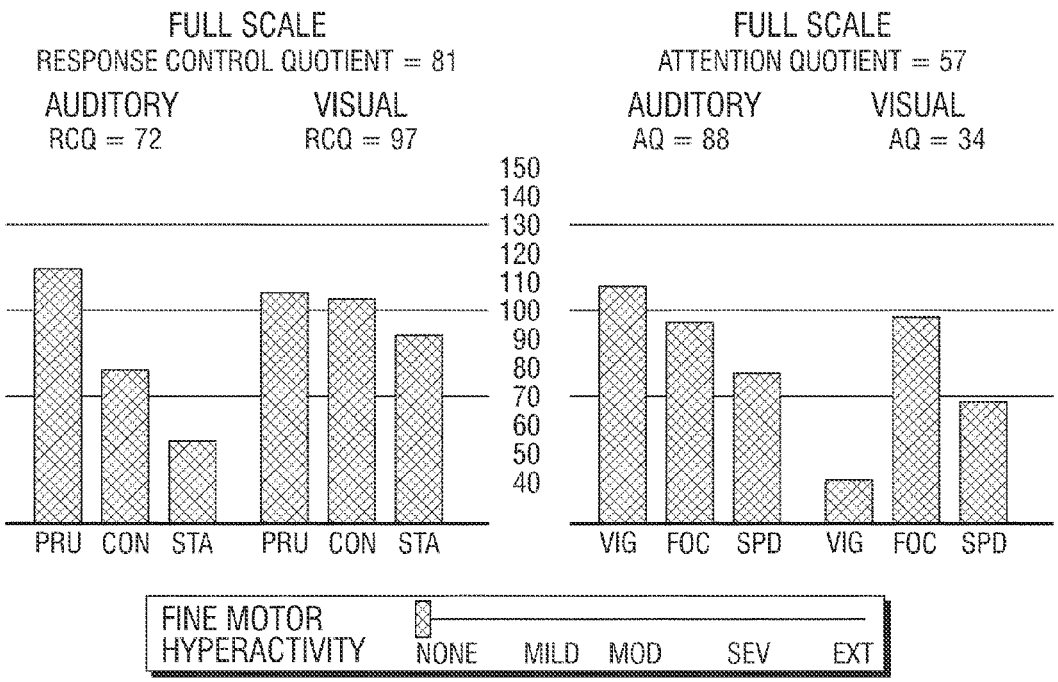
FIGS. 9A-9B show the results of IVA continuous performance without stimulation (A) and with stimulation (B).
Figure 9B:
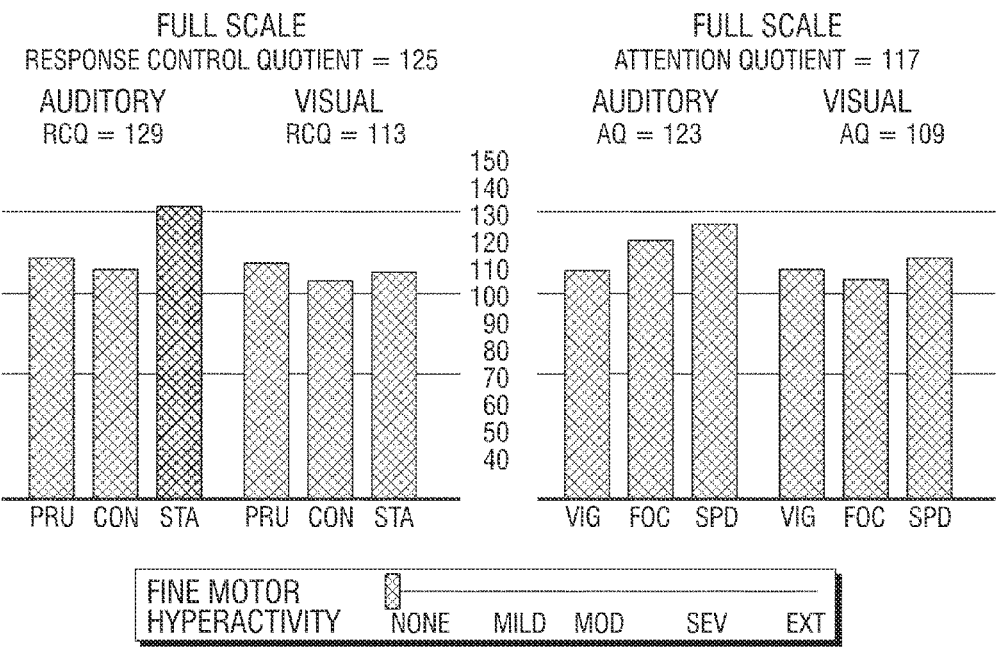

Neuropsychological testing after implant showed a significant improvement on many measures of visual and auditory processing and attentional tasks measured by IVA Continuous Performance (See FIGS. 9A and 9B).

Thus, these results indicated that hyperalgesia through any part of the body was normalized with stimulation, and that even hyperalgesia to light and sound associated with brain injury was treatable with stimulation.

Example 13

Treatment of TBI

A 51 year old man that has suffered from pain for 30 years with multiple head traumas and severe cognitive problems. Prior to stimulation, his Beck Depression Inventory (BDI) was 55 (20+ is considered severely depressed).

A stimulation system was implanted in communication with the C2 dermatome using the system and method for the invention as described herein. After stimulation, his BDI is 2. One of skill in is aware that a score above 20 on a BDI is considered severely depressed and a score of 10 or below is considered within normal limits.

Figure 10A:
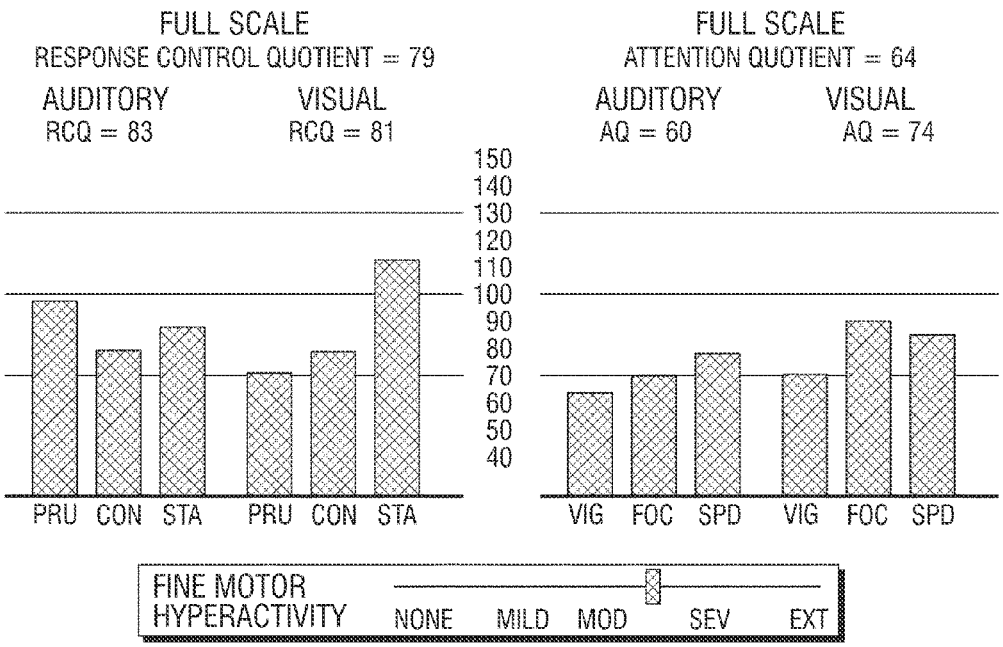
FIGS. 10A-10B show the results of IVA continuous performance without stimulation (A) and with stimulation (B).
Figure 10B:
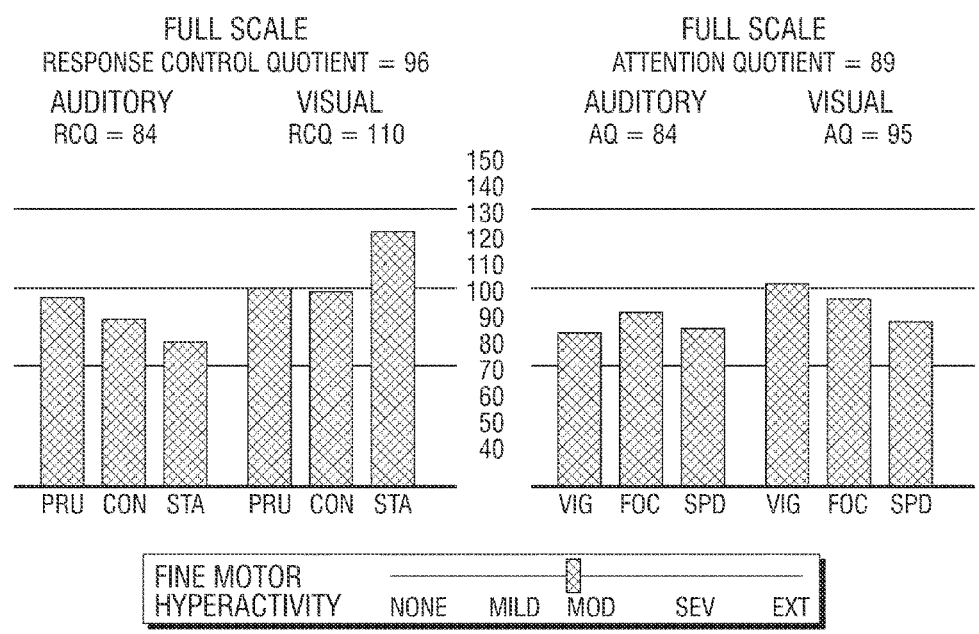

Neuropsychological testing after implant showed a significant improvement on many measures of visual and auditory processing and attentional tasks measured by IVA Continuous Performance (See FIGS. 10A and 10B).

Example 14

Treatment of Obesity

Patient 1

An obese woman that was in a car accident and suffered a TBI was implanted with a stimulation system in communication with the C2 dermatome area using the system and method for the invention as described herein. After stimulation for about one month, the patient lost about 20 pounds. She indicated that she did not have the sense of being hungry, and thus ate smaller meals. Still further, her food choices were also altered. Prior to stimulation, she preferred more fattening food, after implantation of the stimulation system, she preferred healthier food. The patient generally was happier, had an increased mood, decreased pain, increased level of energy, improved sleep, reduced migraines, better or improved coping skills, improved memory, improved personality, for example less anxiety, not depressed and withdrawn.

Patient 2

An obese woman was implanted with a stimulation system in communication with the C2 dermatome area using the system and method for the invention as described herein. After stimulation for about three months, the patient lost about 23 pounds. This patient was not actively trying to loose weight. She indicated that she did not have the sense of being hungry, and thus ate smaller meals. Also, the stimulation alleviated symptoms associated with her fibromyalgia, as well as alleviating her hot flashes and improving her sleep. Still further, this patient also experienced increased mood, for example she was typically irritable and is now calmer.

Patient 3

Figure 11A:
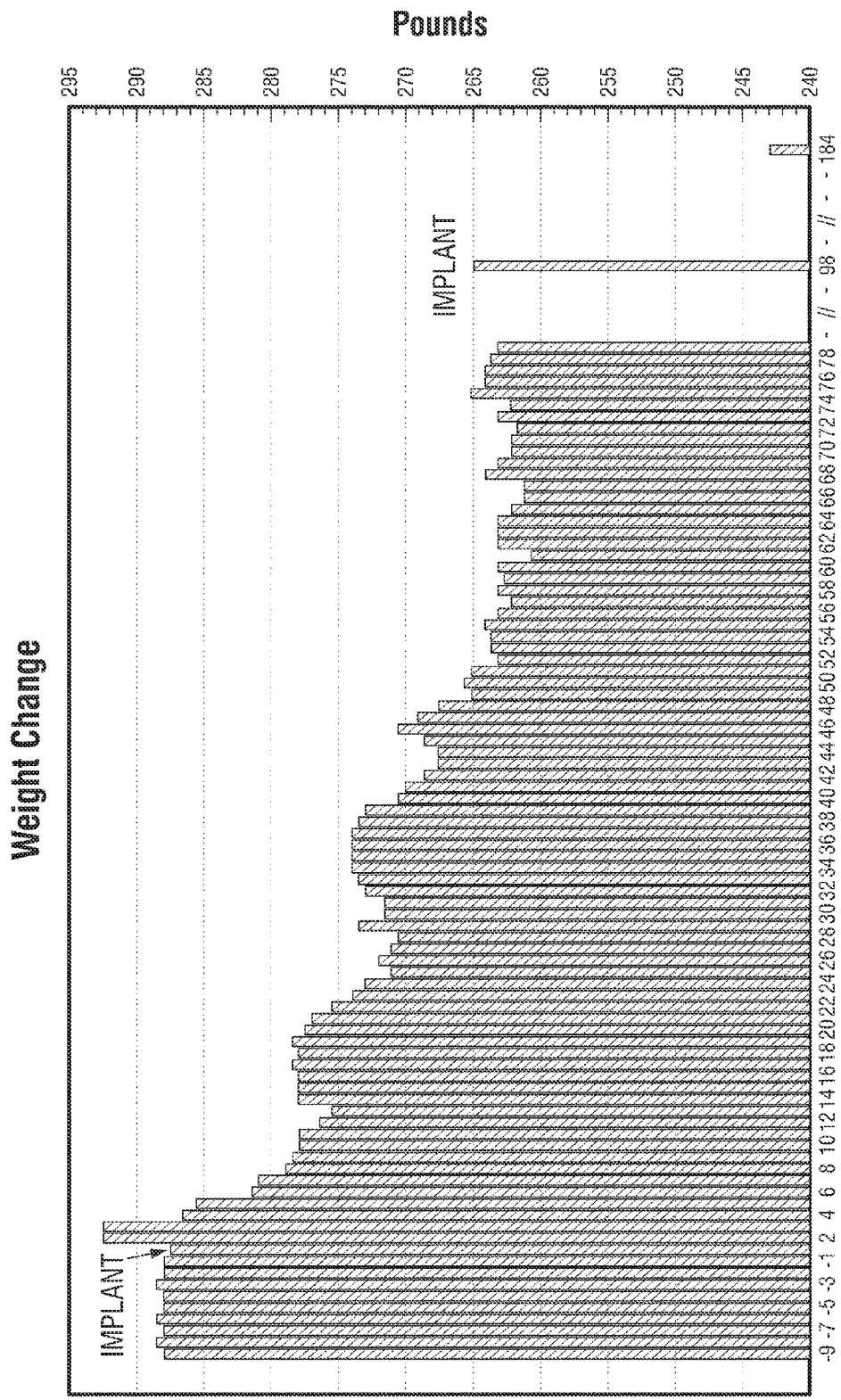
FIGS. 11A-11B show the results of the stimulation system on weight loss.
Figure 11B:
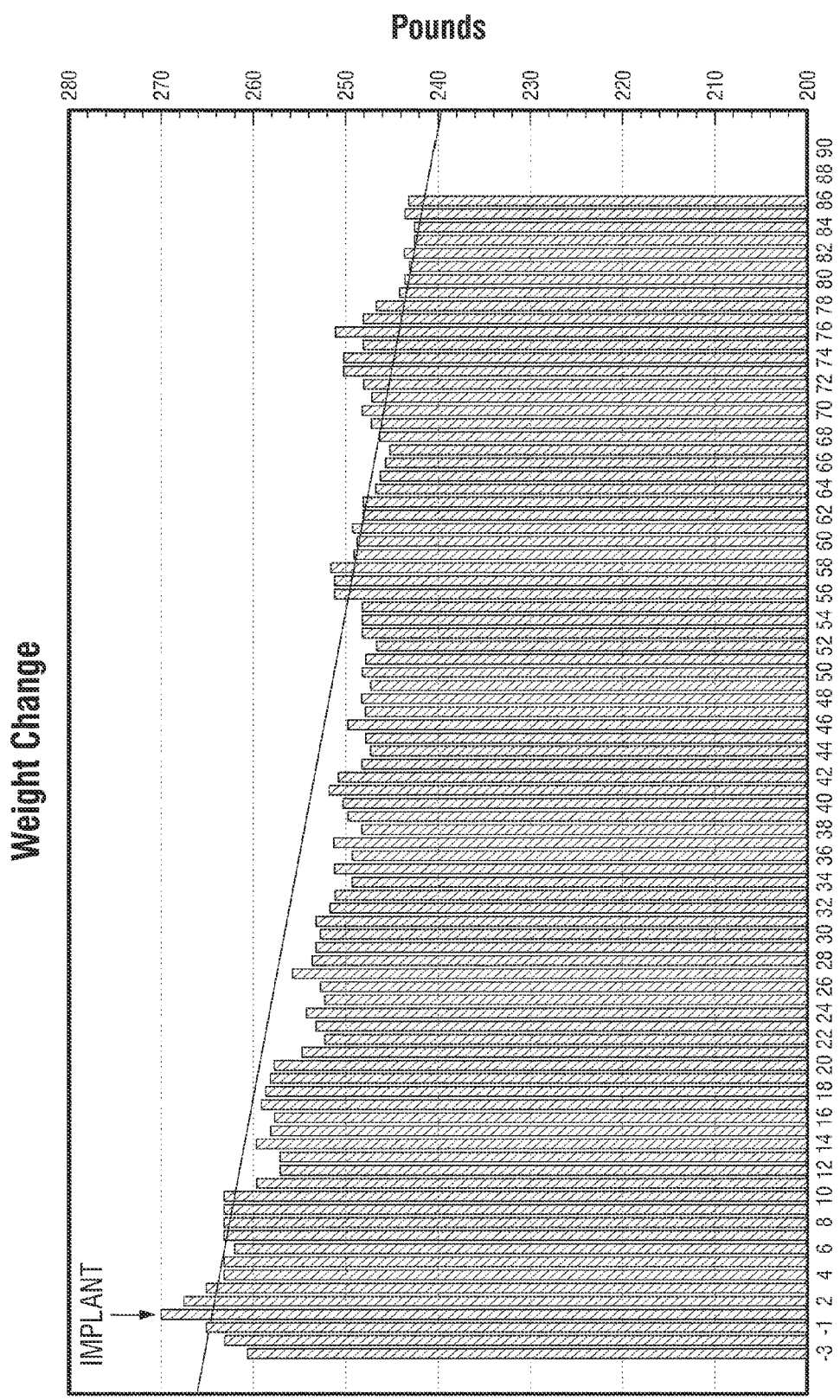

An obese woman was implanted with a stimulation system in communication with the C2 dermatome area using the system and method for the invention as described herein. After stimulation, her daily caloric intake decreased from about 1800 to 1900 calories to about 950 to 1100 calories resulting in weight loss. She indicated that she did not have the sense of being hungry. FIG. 11 shows the weight loss in response to the stimulation of the occipital area. In FIG. 11A, the women was implanted with a trial stimulation system in which the stimulation of the C2 dermatome resulted in the loss of about 30 pounds. After a trail stimulation period, the women was implanted with a permanent implant of which she continued to loose weight, as shown in FIG. 11B. In addition to loosing about 50 pounds, the stimulation also decreased her blood glucose levels, cholesterol levels, decreased blood pressure, and stabilized her hemoglobin levels.

In view of the above, one of skill in the art realizes that the stimulation system of the present invention can be used to treat obesity and symptoms associated therewith such as lipidema, diabetes, as well as alleviating hot flashes and improving sleep.

Example 15

Treatment of Rheumatoid Arthritis

A woman in her early 30's that is suffering from juvenile rheumatoid arthritis was implanted with a stimulation system in communication with the C2 dermatome area using the system and method for the invention as described herein. The stimulation system was implanted for about 6 months during which time the subject's pain was alleviate. Prior to the implant of the stimulation system, the subject would have fluid from her knees drained or removed once a week or once every two weeks. The patient was also receiving weekly injections of methotrexate. The patient also received twice weekly injections of humera. Since the stimulation system has been implanted, the fluid accumulation in the knees has subsided, thus eliminating the necessity of having the knees drained. In addition, the patient stopped taking all medications. Stimulation also improved the range of motion. The stimulation parameters were 3 to about 20 mA, frequency in the range of about 4 to about 30 Hz, and the pulse width is about 20 to about 90 microseconds.

After about 6 months, the patient contracted an infection resulting in the removal of the stimulation system. After the stimulation system was removed, the patient's symptoms returned within a week. Thus, the stimulation system of the present invention alleviated symptoms associated with rheumatoid arthritis, such as pain and swelling, and increased range of motion.

Example 16

Treatment of Chronic Pain and Restless Leg Syndrome

A 75 year old woman who had chronic pain and restless leg syndrome was implanted with the stimulation system of the present invention. Her medications included two neurological drugs for the movement disorder. The stimulation stopped all symptoms of restless legs as well as her pain.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating obesity or an eating disorder in a patient, comprising:
   surgically implanting a stimulation lead with at least one electrode disposed at the back of the patient's head adjacent to occipital nerve tissue such that the at least one electrode is below the skin and above the skull in a C2 dermatome/C3 dermatome area;
   coupling the stimulation lead to a pulse generator;
   operating the pulse generator to generate electrical pulses that stimulate the occipital nerve tissue using the at least one electrode thereby treating the obesity or eating disorder; and
   subsequent to the operating, monitoring improvement in the patient's obesity or eating disorder.

2. The method of claim 1, wherein the stimulation lead comprises a plurality of electrodes.

3. The method of claim 1, wherein the electrical pulses comprise an amplitude in the range of about 2 mA to about 100 mA, a frequency in the range of about 3 Hz to about 50 Hz, and a pulse width in the range of about 5 µs to about 100 µs.

4. The method of claim 1, wherein the eating disorder is anorexia nervosa.

5. The method of claim 1, wherein the eating disorder is accompanied by a mood or anxiety disorder.

6. The method of claim 5, wherein the mood or anxiety disorder is depression.

7. The method of claim 1, wherein the eating disorder is accompanied by Crohn's disease or irritable bowel syndrome.

8. The method of claim 1, wherein the stimulation lead is a percutaneous lead.

9. The method of claim 1, wherein the stimulation lead is a laminotomy, paddle, or surgical lead.

* * * * *